United States Patent
Truckai et al.

(10) Patent No.: US 10,758,300 B2
(45) Date of Patent: *Sep. 1, 2020

(54) METHODS FOR ENDOMETRIAL ABLATION

(71) Applicant: Minerva Surgical, Inc., Cupertino, CA (US)

(72) Inventors: Csaba Truckai, Saratoga, CA (US); Akos Toth, Cupertino, CA (US)

(73) Assignee: Minerva Surgical, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/885,854

(22) Filed: Oct. 16, 2015

(65) Prior Publication Data

US 2016/0296277 A1    Oct. 13, 2016

Related U.S. Application Data

(63) Continuation of application No. 13/667,774, filed on Nov. 2, 2012, now Pat. No. 9,186,208, which is a
(Continued)

(51) Int. Cl.
*A61B 18/14*    (2006.01)
*A61B 18/04*    (2006.01)
(Continued)

(52) U.S. Cl.
CPC ........ *A61B 18/1485* (2013.01); *A61B 18/042* (2013.01); *A61B 2017/4216* (2013.01); *A61B 2018/00232* (2013.01); *A61B 2018/00559* (2013.01); *A61B 2018/00577* (2013.01); *A61B 2018/00791* (2013.01);
(Continued)

(58) Field of Classification Search
USPC ....................................................... 607/138
See application file for complete search history.

(56) References Cited

U.S. PATENT DOCUMENTS

| 4,611,604 A | 9/1986 | Botvidsson et al. |
| 4,979,948 A | 12/1990 | Geddes et al. |

(Continued)

FOREIGN PATENT DOCUMENTS

WO    WO 95/10981 A1    4/1995

OTHER PUBLICATIONS

International search report and written opinion dated Jan. 12, 2012 for PCT/US2011/055815.
(Continued)

*Primary Examiner* — Kennedy Schaetzle
(74) *Attorney, Agent, or Firm* — Wilson, Sonsini Goodrich & Rosati

(57) ABSTRACT

A method for ablating a uterine endometrium enlarges an expandable-contractible frame to expand a compliant energy-delivery surface into a planar triangular shape and engage the surface against the walls of a patient's uterine cavity. The frame has flexible outer elements in lateral contact with the compliant surface and flexible inner elements not in said lateral contact, wherein the inner flexible element and outer flexible elements have substantially dissimilar material properties. Energy is applied through the compliant energy-delivery surface to ablate the endometrium.

23 Claims, 25 Drawing Sheets

Related U.S. Application Data continuation-in-part of application No. 13/267,258, filed on Oct. 6, 2011.

(60) Provisional application No. 61/394,693, filed on Oct. 19, 2010, provisional application No. 61/556,675, filed on Nov. 7, 2011.

(51) Int. Cl.
*A61B 17/42* (2006.01)
*A61B 18/00* (2006.01)
*A61B 18/16* (2006.01)

(52) U.S. Cl.
CPC . *A61B 2018/147* (2013.01); *A61B 2018/1412* (2013.01); *A61B 2018/1465* (2013.01); *A61B 2018/162* (2013.01)

(56) References Cited

U.S. PATENT DOCUMENTS

| | | | |
|---|---|---|---|
| 5,105,808 A | 4/1992 | Neuwirth et al. | |
| 5,191,883 A | 3/1993 | Lennox et al. | |
| 5,277,201 A | 1/1994 | Stern | |
| 5,549,546 A | 8/1996 | Schneider et al. | |
| 5,769,880 A | 6/1998 | Truckai et al. | |
| 5,891,134 A | 4/1999 | Goble et al. | |
| 5,925,038 A | 7/1999 | Panescu et al. | |
| 6,041,260 A | 3/2000 | Stern et al. | |
| 6,099,524 A * | 8/2000 | Lipson | A61B 5/0422 606/41 |
| 6,296,639 B1 | 10/2001 | Truckai et al. | |
| 6,663,626 B2 | 12/2003 | Truckai et al. | |
| 6,736,811 B2 | 5/2004 | Panescu et al. | |
| 6,813,520 B2 | 11/2004 | Truckai et al. | |
| 7,371,231 B2 | 5/2008 | Rioux et al. | |
| 8,394,037 B2 | 3/2013 | Toth et al. | |
| 8,500,732 B2 | 8/2013 | Truckai et al. | |
| 8,529,562 B2 | 9/2013 | Vissy et al. | |
| 8,715,278 B2 | 5/2014 | Toth et al. | |
| 9,186,208 B2 * | 11/2015 | Truckai | A61B 18/1485 |
| 2002/0022870 A1 | 2/2002 | Truckai et al. | |
| 2005/0143728 A1 | 6/2005 | Sampson et al. | |
| 2005/0240211 A1 | 10/2005 | Sporri et al. | |
| 2007/0083193 A1 * | 4/2007 | Werneth | A61B 5/742 606/41 |
| 2008/0097425 A1 | 4/2008 | Truckai | |
| 2008/0167664 A1 | 7/2008 | Payne et al. | |
| 2008/0275445 A1 | 11/2008 | Kelly et al. | |
| 2009/0054892 A1 | 2/2009 | Rioux et al. | |
| 2010/0100091 A1 | 4/2010 | Truckai | |
| 2011/0118718 A1 * | 5/2011 | Toth | A61B 5/1076 606/33 |
| 2012/0265197 A1 | 10/2012 | Truckai et al. | |
| 2013/0304060 A1 | 11/2013 | Truckai et al. | |

OTHER PUBLICATIONS

Notice of allowance dated Jul. 24, 2015 for U.S. Appl. No. 13/667,774.
Office action dated Feb. 20, 2015 for U.S. Appl. No. 13/267,258.
Office action dated Mar. 19, 2015 for U.S. Appl. No. 13/667,774.
Office action dated Jul. 7, 2014 for U.S. Appl. No. 13/267,258.
Office action dated Sep. 24, 2014 for U.S. Appl. No. 13/667,774.
Third party observations dated Sep. 6, 2013 for EP Application No. 10830743.0.

* cited by examiner

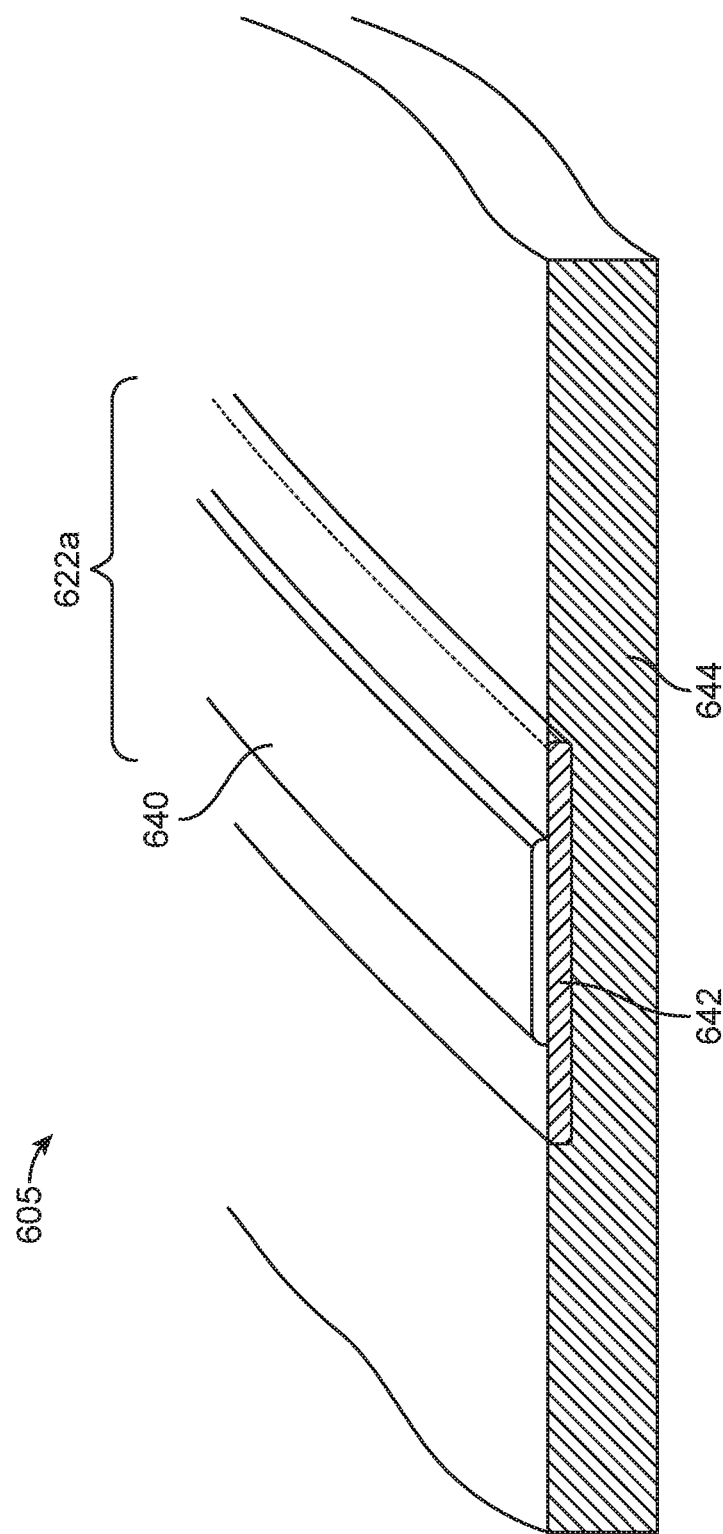

METHODS FOR ENDOMETRIAL ABLATION

CROSS REFERENCE TO RELATED APPLICATIONS

This application is a continuation of U.S. patent application Ser. No. 13/667,774, filed Nov. 2, 2012, which is a continuation-in-part of U.S. patent application Ser. No. 13/267,258, filed Oct. 6, 2011, which claims the benefit of Provisional Application No. 61/394,693, filed Oct. 19, 2010; this application also claims priority to Provisional Application No. 61/556,675, filed Nov. 7, 2011, the entire contents of each are incorporated herein by reference.

The specification of this provisional application includes FIGS. 1-20 and the associated text from non-provisional application Ser. No. 13/267,258, the full disclosure of which is incorporated herein by reference. The non-provisional filing of this provisional application may be a continuation-in-part of application Ser. No. 13/267,258.

BACKGROUND OF THE INVENTION

1. Field of the Invention

The present invention relates to electrosurgical methods and devices for global endometrial ablation in a treatment of menorrhagia. More particularly, the present invention relates to applying radiofrequency current to endometrial tissue by means of capacitively coupling the current through an expandable, thin-wall dielectric member enclosing an ionized gas.

A variety of devices have been developed or proposed for endometrial ablation. Of relevance to the present invention, a variety of radiofrequency ablation devices have been proposed including solid electrodes, balloon electrodes, metalized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. Nos. 6,736,811 and 5,925,038 show an inflatable conductive electrode.

BRIEF SUMMARY OF THE INVENTION

The present invention provides methods and systems for performing endometrial ablation for the treatment uterine diseases in human females. In a first aspect, the present invention provides systems for endometrial ablation where the systems comprise a shaft with an expandable-contractible frame mounted thereon. A compliant energy-delivery surface is carried by the frame, and the surface defines an interior chamber when expanded by the frame. The frame is configured to engage the surface against an interior wall or other portion of the patient's uterine cavity when the working end of the shaft is inserted into the cavity and the frame is expanded. The exterior surface carries an electrode in order to delivery energy into the uterine wall for ablation or other therapeutic use.

In an exemplary embodiment, the system is configured so that the expandable-contractible frame provides a primary or initial expansion of the compliant energy-delivery surface in a lateral direction by expanding the frame within the interior chamber. The system is preferably further configured to provide for a secondary expansion of the energy-delivery surface by inflating the interior chamber to cause the surface to expand in an anterior-posterior direction, i.e. a direction which is generally perpendicular or normal to the lateral direction defined by the frame when it opens.

In a second aspect of the present invention, the energy-delivery surface comprises a thin-walled elastomer, such as a silicone elastomer, where the electrode structure is optionally molded into the outer surface of the elastomer. The thin-walled elastomer preferably circumscribes the expandable-contractible frame to define the interior chamber therein when the frame is expanded. Such structure is particularly suitable for the two-stage expansion described above where the frame first expands the elastomeric chamber laterally and an inflation of the chamber expands the wall of the chamber in an anterior-posterior direction.

The systems of the present invention may further comprise a fluid pressure source coupled to the interior chamber. The systems may still further comprise at least one temperature sensor carried on or near the energy-delivery surface. The systems will usually also comprise a controller operatively coupled to the temperature sensor and/or the fluid pressure source. The controller allows automatic and/or manual control of inflation and/or energy delivery protocols for therapeutic treatments according to the present invention.

Methods according to the present invention for treating a patient's uterus comprise positioning a probe in the patient's uterine cavity, typically by trans-cervically introducing the probe or, alternatively, by laparoscopic or other minimally invasive introduction techniques. A probe end is then expanded in a primary or first direction by actuating a frame within an anterior portion of the probe end. The probe end is then expanded in a second direction by introducing a fluid medium into the interior chamber. The twice-expanded probe end may then be used to deliver energy into the uterine cavity, typically into a wall of the uterine cavity to achieve therapeutic ablation. The delivered energy may be radiofrequency (RF) energy which is delivered from one or a plurality of electrodes present on the expanded surface, usually an exterior surface of the balloon. The RF energy may be monopolar or may be delivered by bipolar electrodes carried by the probe end. Alternatively, the energy may be delivered by capacitive coupling of a current delivered through the probe end. The first direction of the balloon expansion is preferably in a direction laterally across the uterine cavity and is typically achieved by frame actuation while the second direction is usually achieved by inflation of the probe end and lies in a direction along an anterior-posterior axis.

In a further method according to the present invention, endometrial ablation is performed by trans-cervical introduction of a probe working end into a patient's uterine cavity. The probe working end comprises an expandable-contractible frame which carries a compliant energy-delivery surface. The frame is actuated to expand the energy-deliver surface within the uterine cavity, and an inflation medium is then delivered to an interior chamber within the working end to further expand the energy delivery surface. Energy is delivered from the energy-delivery surface in order to effect the desired endometrial ablation or other therapeutic treatment. Usually, the frame expands the energy-delivery surface in the a plane which is generally laterally oriented within the uterus, while inflation expands the surface in a direction generally transverse to a lateral direction, i.e., in an anterior-posterior direction. The inflation source will typically deliver a very low inflation pressure, usually above 20 mm Hg (in the range from 20 mm Hg to 100 mm Hg), sometimes above 30 mm Hg (in the range from 30 mm Hg to 100 mm Hg), often above 40 mm Hg (in the range from 40 mm Hg to 100 mm Hg), and occasionally over 50 mm Hg (in the range from 50 mm Hg to 100 mm Hg). Such low inflation levels have been found to be sufficient to expand the working end of the probes to fully engage the energy-delivery surface against the wall of the uterine cavity and provide efficient energy delivery, from electrode contact, inductive current coupling, or other energy delivery modes. In specific embodiments, an inflation chamber within the working end surrounded by a thin-walled elastomer is created by circulating a gas stream within the chamber under conditions which maintain a pressure in the interior chamber within the ranges set forth above.

In yet a further aspect of the present invention, a method for performing endometrial ablation comprises trans-cervically introducing a probe working end into a patient's uterine cavity. A thin-walled energy-delivery surface on the working end is then expanded within the uterine cavity, and energy is delivered from the expanded surface to cause endometrial ablation. The depth of ablation may then be monitored by an ultrasonic transducer which is carried by or within the working end of the probe.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 15 is an enlarged sectional view of the flex-circuit electrode integrated into an expandable surface of the working end of FIG. 14A.

DETAILED DESCRIPTION

In general, an electrosurgical ablation system is described herein that comprises an elongated introducer member for accessing a patient's uterine cavity with a working end that deploys an expandable thin-wall dielectric structure containing an electrically non-conductive gas as a dielectric. In one embodiment, an interior chamber of the thin-wall dielectric structure contains a circulating neutral gas such as argon. An RF power source provides current that is coupled to the neutral gas flow by a first polarity electrode disposed within the interior chamber and a second polarity electrode at an exterior of the working end. The gas flow, which is converted to a conductive plasma by an electrode arrangement, functions as a switching mechanism that permits current flow to engaged endometrial tissue only when the voltage across the combination of the gas, the thin-wall dielectric structure and the engaged tissue reaches a threshold that causes capacitive coupling across the thin-wall dielectric material. By capacitively coupling current to tissue in this manner, the system provides a substantially uniform tissue effect within all tissue in contact with the expanded dielectric structure. Further, the invention allows the neutral gas to be created contemporaneously with the capacitive coupling of current to tissue.

In general, this disclosure may use the terms "plasma," "conductive gas" and "ionized gas" interchangeably. A plasma consists of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

Figure 1:
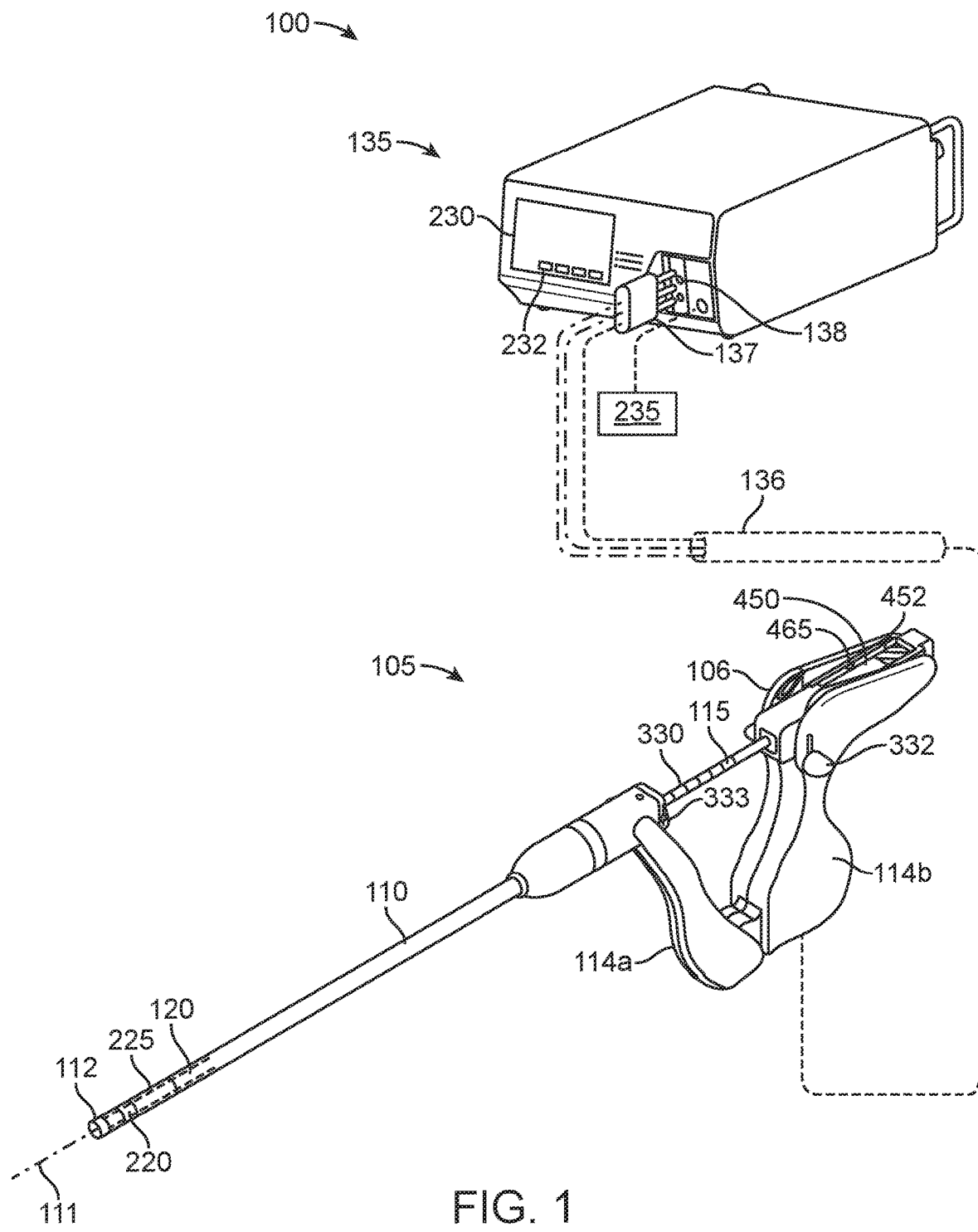
FIG. 1 is a perspective view of an ablation system corresponding to the invention, including a hand-held electrosurgical device for endometrial ablation, RF power source, gas source and controller.
Figure 2:
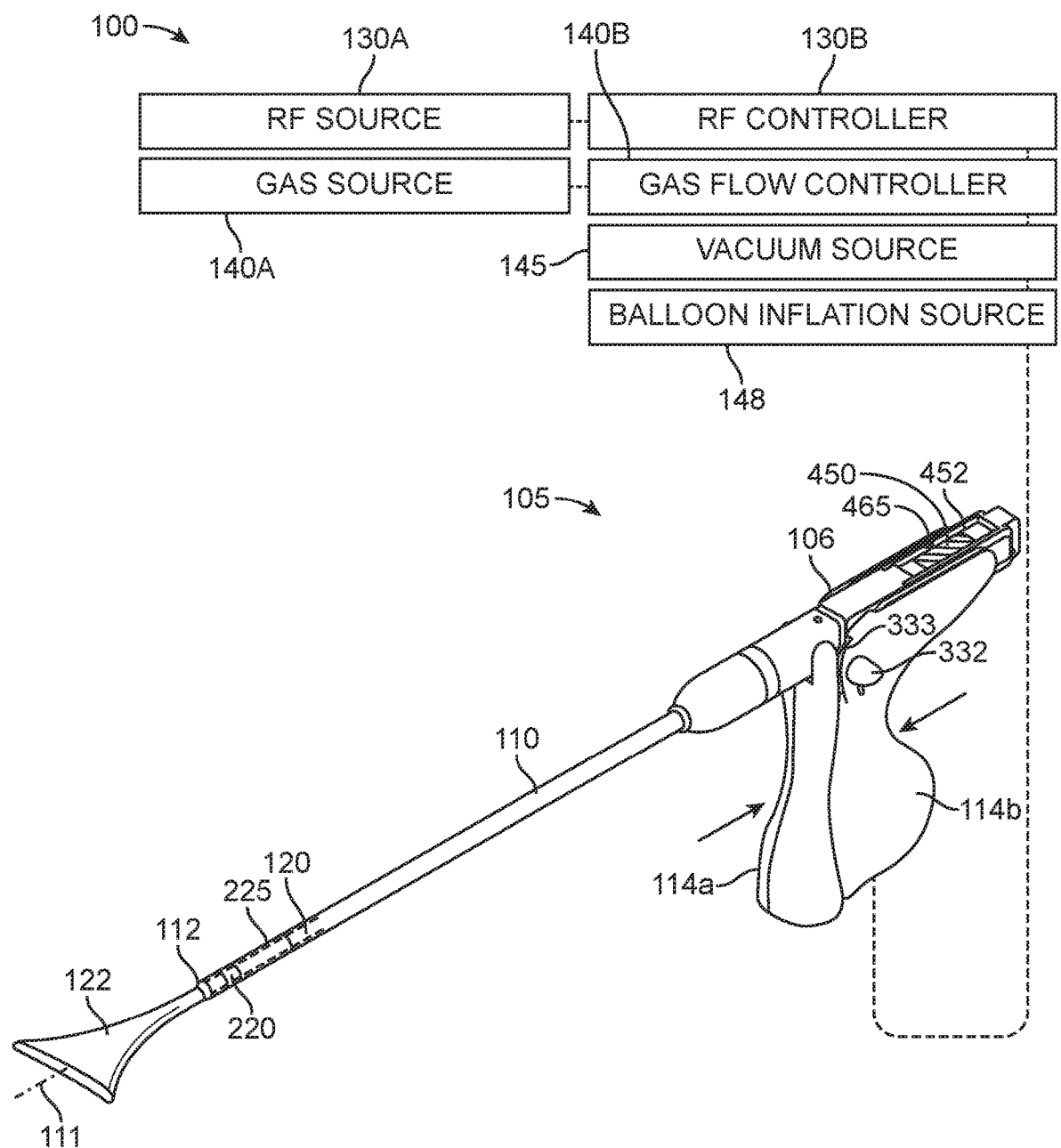
FIG. 2 is a view of the hand-held electrosurgical device of FIG. 1 with a deployed, expanded thin-wall dielectric structure.

FIG. 1 depicts one embodiment of an electrosurgical ablation system 100 configured for endometrial ablation. The system 100 includes a hand-held apparatus 105 with a proximal handle 106 shaped for grasping with a human hand that is coupled to an elongated introducer sleeve 110 having axis 111 that extends to a distal end 112. The introducer sleeve 110 can be fabricated of a thin-wall plastic, composite, ceramic or metal in a round or oval cross-section having a diameter or major axis ranging from about 4 mm to 8 mm in at least a distal portion of the sleeve that accesses the uterine cavity. The handle 106 is fabricated of an electrically insulative material such as a molded plastic with a pistol-grip having first and second portions, 114a and 114b, that can be squeezed toward one another to translate an elongated translatable sleeve 115 which is housed in a bore 120 in the elongated introducer sleeve 110. By actuating the first and second handle portions, 114a and 114b, a working end 122 can be deployed from a first retracted position (FIG. 1) in the distal portion of bore 120 in introducer sleeve 110 to an extended position as shown in FIG. 2. In FIG. 2, it can be seen that the first and second handle portions, 114a and 114b, are in a second actuated position with the working end 122 deployed from the bore 120 in introducer sleeve 110.

Figure 3:
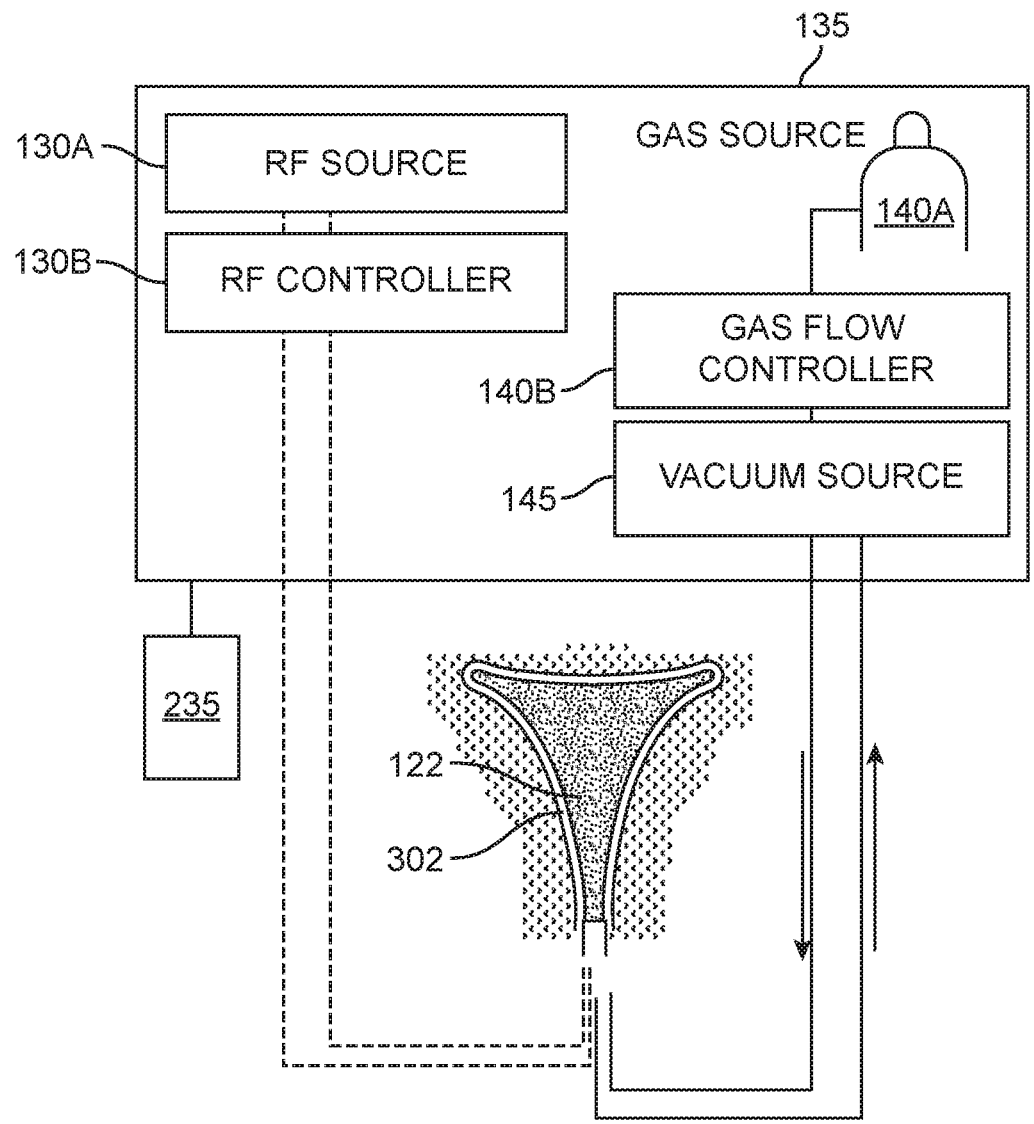
FIG. 3 is a block diagram of components of one electrosurgical system corresponding to the invention.

FIGS. 2 and 3 shows that ablation system 100 includes an RF energy source 130A and RF controller 130B in a control unit 135. The RF energy source 130A is connected to the hand-held device 105 by a flexible conduit 136 with a plug-in connector 137 configured with a gas inflow channel, a gas outflow channel, and first and second electrical leads for connecting to receiving connector 138 in the control unit 135. The control unit 135, as will be described further below in FIGS. 3 and 4, further comprises a neutral gas inflow source 140A, gas flow controller 140B and optional vacuum or negative pressure source 145 to provide controlled gas inflows and gas outflows to and from the working end 122. The control unit 135 further includes a balloon inflation source 148 for inflating an expandable sealing balloon 225 carried on introducer sleeve 110 as described further below.

Referring to FIG. 2, the working end 122 includes a flexible, thin-wall member or structure 150 of a dielectric material that when expanded has a triangular shape configured for contacting the patient's endometrial lining that is targeted for ablation. In one embodiment as shown in FIGS. 2, 5 and 6, the dielectric structure 150 comprises a thin-wall material such as silicone with a fluid-tight interior chamber 152.

In an embodiment, an expandable-collapsible frame assembly 155 is disposed in the interior chamber. Alternatively, the dielectric structure may be expanded by a neutral gas without a frame, but using a frame offers a number of advantages. First, the uterine cavity is flattened with the opposing walls in contact with one another. Expanding a balloon-type member may cause undesirable pain or spasms. For this reason, a flat structure that is expanded by a frame is better suited for deployment in the uterine cavity. Second, in embodiments herein, the neutral gas is converted to a conductive plasma at a very low pressure controlled by gas inflows and gas outflows—so that any pressurization of a balloon-type member with the neutral gas may exceed a desired pressure range and would require complex controls of gas inflows and gas outflows. Third, as described below, the frame provides an electrode for contact with the neutral gas in the interior chamber 152 of the dielectric structure 150, and the frame 155 extends into all regions of the interior chamber to insure electrode exposure to all regions of the neutral gas and plasma. The frame 155 can be constructed of any flexible material with at least portions of the frame functioning as spring elements to move the thin-wall structure 150 from a collapsed configuration (FIG. 1) to an expanded, deployed configuration (FIG. 2) in a patient's uterine cavity. In one embodiment, the frame 155 comprises stainless steel elements 158a, 158b and 160a and 160b that function akin to leaf springs. The frame can be a stainless steel such as 316 SS, 17A SS, 420 SS, 440 SS or the frame can be a NiTi material. The frame preferably extends along a single plane, yet remains thin transverse to the plane, so that the frame may expand into the uterine cavity. The frame elements can have a thickness ranging from about 0.005" to 0.025". As can be seen in FIGS. 5 and 6, the proximal ends 162*a* and 162*b* of spring elements 158*a*, 158*b* are fixed (e.g., by welds 164) to the distal end 165 of sleeve member 115. The proximal ends 166*a* and 166*b* of spring elements 160*a*, 160*b* are welded to distal portion 168 of a secondary translatable sleeve 170 that can be extended from bore 175 in translatable sleeve 115. The secondary translatable sleeve 170 is dimensioned for a loose fit in bore 175 to allow gas flows within bore 175. FIGS. 5 and 6 further illustrate the distal ends 176*a* and 176*b* of spring elements 158*a*, 158*b* are welded to distal ends 178*a* and 178*b* of spring elements 160*a* and 160*b* to thus provide a frame 155 that can be moved from a linear shape (see FIG. 1) to an expanded triangular shape (FIGS. 5 and 6).

As will be described further below, the bore 175 in sleeve 115 and bore 180 in secondary translatable sleeve 170 function as gas outflow and gas inflow lumens, respectively. It should be appreciated that the gas inflow lumen can comprise any single lumen or plurality of lumens in either sleeve 115 or sleeve 170 or another sleeve, or other parts of the frame 155 or the at least one gas flow lumen can be formed into a wall of dielectric structure 150. In FIGS. 5, 6 and 7 it can be seen that gas inflows are provided through bore 180 in sleeve 170, and gas outflows are provided in bore 175 of sleeve 115. However, the inflows and outflows can be also be reversed between bores 175 and 180 of the various sleeves. FIGS. 5 and 6 further show that a rounded bumper element 185 is provided at the distal end of sleeve 170 to insure that no sharp edges of the distal end of sleeve 170 can contact the inside of the thin dielectric wall 150. In one embodiment, the bumper element 185 is silicone, but it could also comprise a rounded metal element. FIGS. 5 and 6 also show that a plurality of gas inflow ports 188 can be provided along a length of in sleeve 170 in chamber 152, as well as a port 190 in the distal end of sleeve 170 and bumper element 185. The sectional view of FIG. 7 also shows the gas flow passageways within the interior of introducer sleeve 110.

Figure 5:
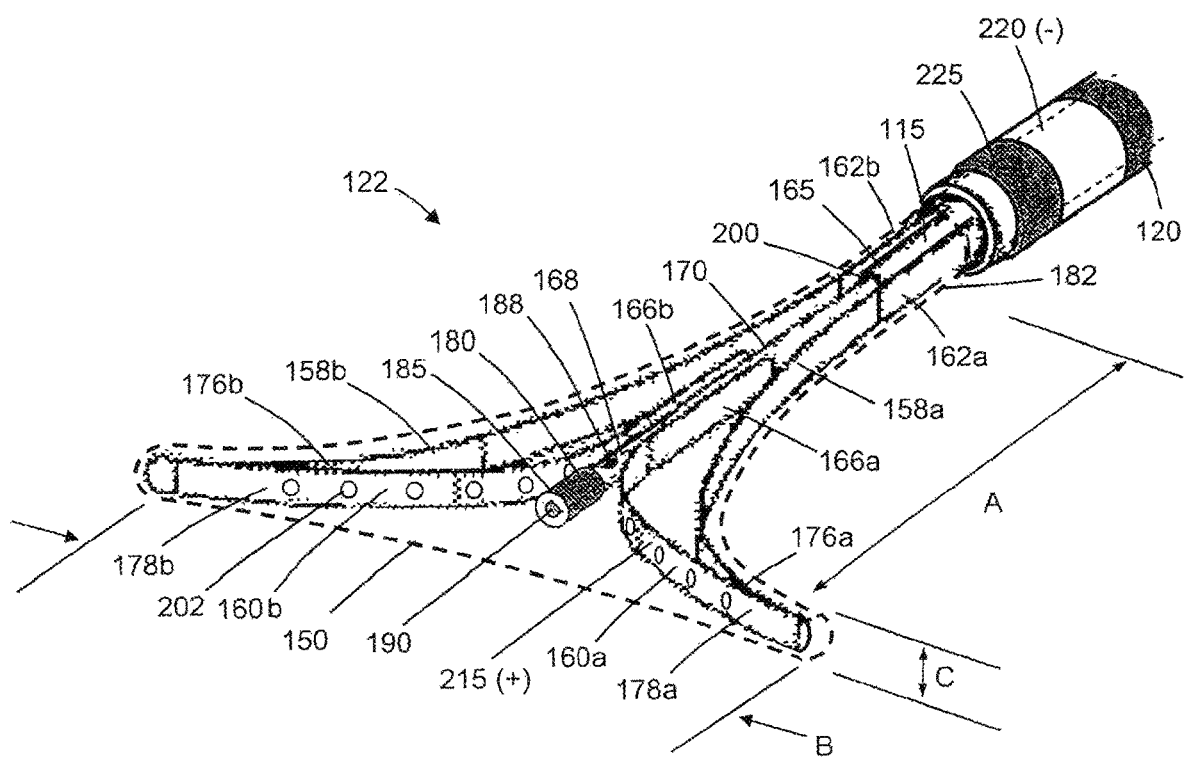
FIG. 5 is an enlarged perspective view of the expanded thin-wall dielectric structure, showing an expandable-collapsible frame with the thin dielectric wall in phantom view.
Figure 6:
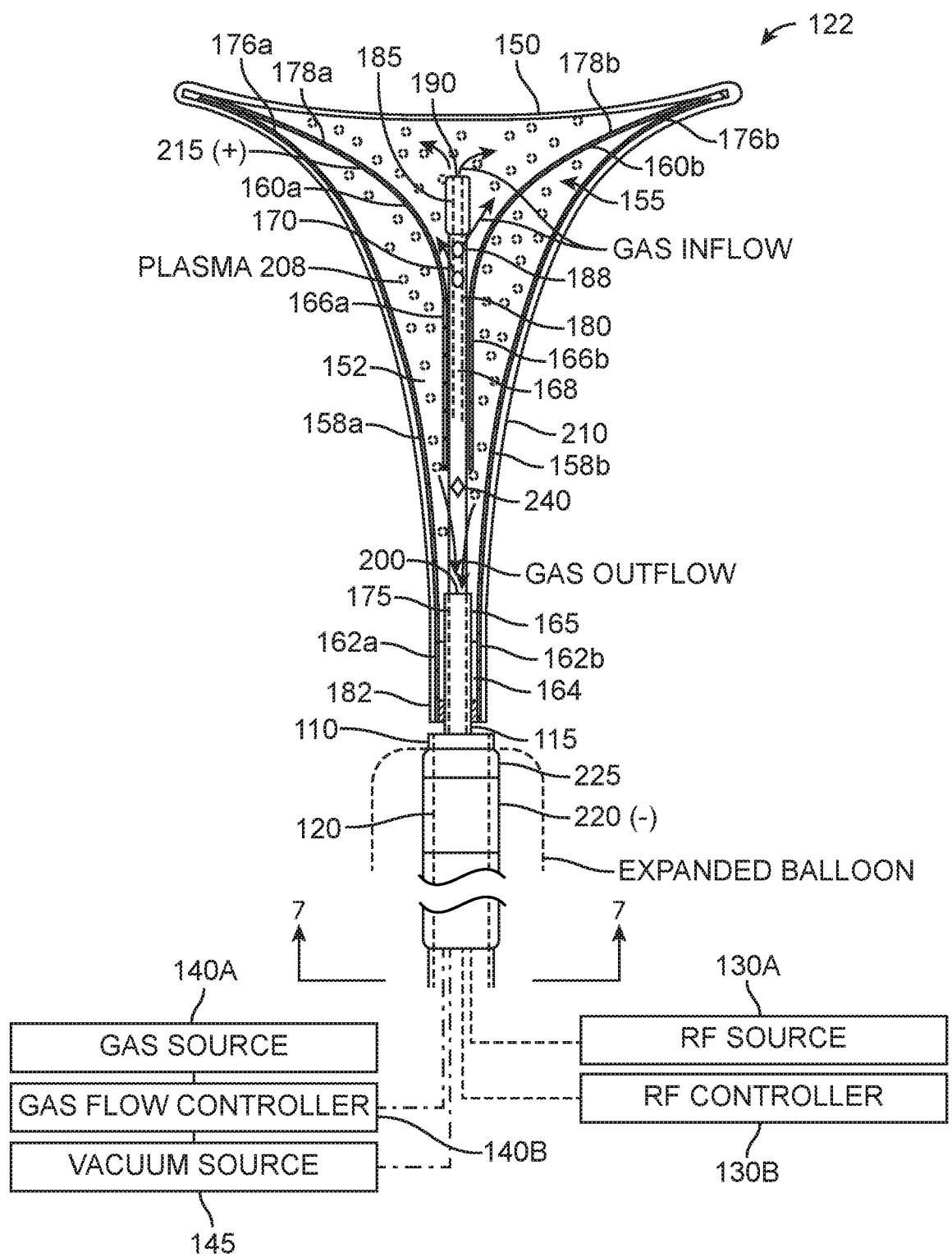
FIG. 6 is a partial sectional view of the expanded thin-wall dielectric structure of FIG. 5 showing (i) translatable members of the expandable-collapsible frame a that move the structure between collapsed and (ii) gas inflow and outflow lumens.
Figure 7:
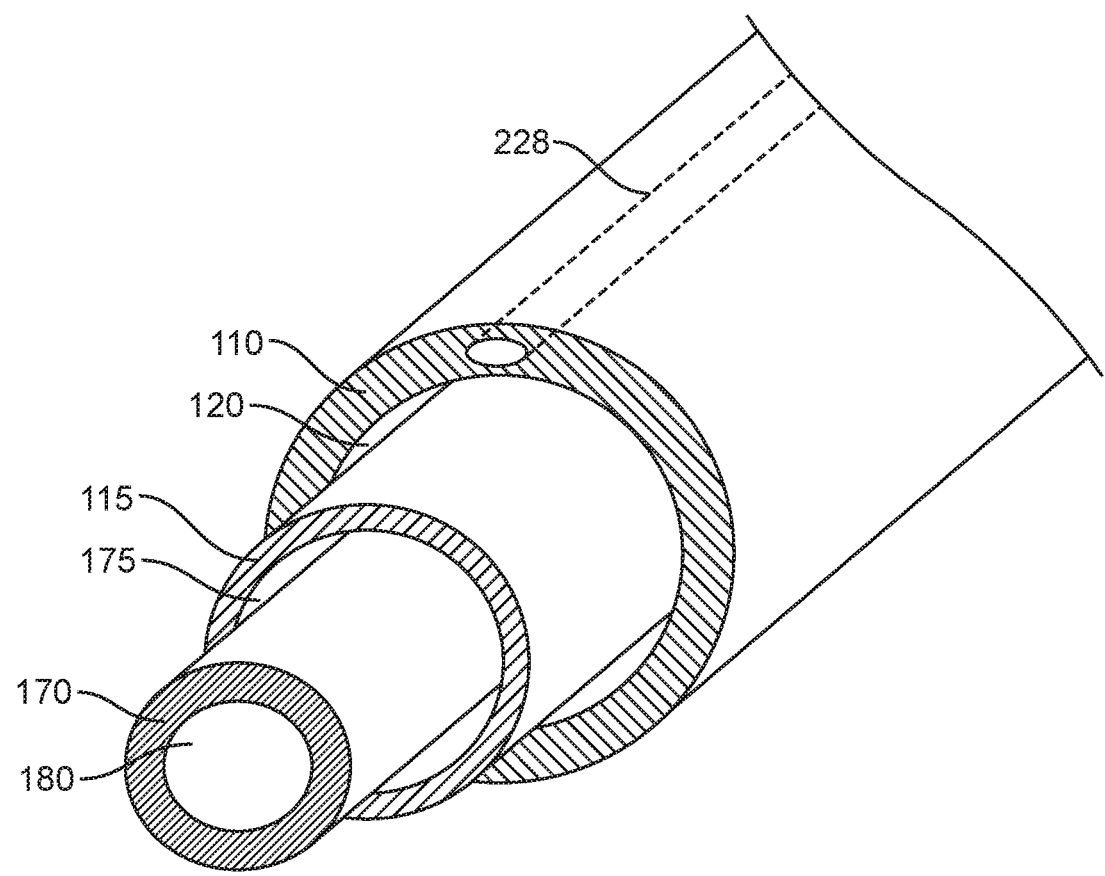
FIG. 7 is a sectional view of an introducer sleeve showing various lumens of the introducer sleeve taken along line 7-7 of FIG. 6.

It can be understood from FIGS. 1, 2, 5 and 6 that actuation of first and second handle portions, 114*a* and 114*b*, (i) initially causes movement of the assembly of sleeves 115 and 170 relative to bore 120 of introducer sleeve 110, and (ii) secondarily causes extension of sleeve 170 from bore 175 in sleeve 115 to expand the frame 155 into the triangular shape of FIG. 5. The dimensions of the triangular shape are suited for a patient uterine cavity, and for example can have an axial length A ranging from 4 to 10 cm and a maximum width B at the distal end ranging from about 2 to 5 cm. In one embodiment, the thickness C of the thin-wall structure 150 can be from 1 to 4 mm as determined by the dimensions of spring elements 158*a*, 158*b*, 160*a* and 160*b* of frame assembly 155. It should be appreciated that the frame assembly 155 can comprise round wire elements, flat spring elements, of any suitable metal or polymer that can provide opening forces to move thin-wall structure 150 from a collapsed configuration to an expanded configuration within the patient uterus. Alternatively, some elements of the frame 155 can be spring elements and some elements can be flexible without inherent spring characteristics.

As will be described below, the working end embodiment of FIGS. 2, 5 and 6 has a thin-wall structure 150 that is formed of a dielectric material such as silicone that permits capacitive coupling of current to engaged tissue while the frame assembly 155 provides structural support to position the thin-wall structure 150 against tissue. Further, gas inflows into the interior chamber 152 of the thin-wall structure can assist in supporting the dielectric wall so as to contact endometrial tissue. The dielectric thin-wall structure 150 can be free from fixation to the frame assembly 155, or can be bonded to an outward-facing portion or portions of frame elements 158*a* and 158*b*. The proximal end 182 of thin-wall structure 150 is bonded to the exterior of the distal end of sleeve 115 to thus provide a sealed, fluid-tight interior chamber 152 (FIG. 5).

In one embodiment, the gas inflow source 140A comprises one or more compressed gas cartridges that communicate with flexible conduit 136 through plug-in connector 137 and receiving connector 138 in the control unit 135 (FIGS. 1-2). As can be seen in FIGS. 5-6, the gas inflows from source 140A flow through bore 180 in sleeve 170 to open terminations 188 and 190 therein to flow into interior chamber 152. A vacuum source 145 is connected through conduit 136 and connector 137 to allow circulation of gas flow through the interior chamber 152 of the thin-wall dielectric structure 150. In FIGS. 5 and 6, it can be seen that gas outflows communicate with vacuum source 145 through open end 200 of bore 175 in sleeve 115. Referring to FIG. 5, it can be seen that frame elements 158*a* and 158*b* are configured with a plurality of apertures 202 to allow for gas flows through all interior portions of the frame elements, and thus gas inflows from open terminations 188, 190 in bore 180 are free to circulated through interior chamber 152 to return to an outflow path through open end 200 of bore 175 of sleeve 115. As will be described below (see FIGS. 3-4), the gas inflow source 140A is connected to a gas flow or circulation controller 140B which controls a pressure regulator 205 and also controls vacuum source 145 which is adapted for assisting in circulation of the gas. It should be appreciated that the frame elements can be configured with apertures, notched edges or any other configurations that allow for effective circulation of a gas through interior chamber 152 of the thin-wall structure 150 between the inflow and outflow passageways.

Now turning to the electrosurgical aspects of the invention, FIGS. 5 and 6 illustrate opposing polarity electrodes of the system 100 that are configured to convert a flow of neutral gas in chamber 152 into a plasma 208 (FIG. 6) and to allow capacitive coupling of current through a wall 210 of the thin-wall dielectric structure 150 to endometrial tissue in contact with the wall 210. The electrosurgical methods of capacitively coupling RF current across a plasma 208 and dielectric wall 210 to cause Joule heating in tissue and to conductively heat tissue from the dielectric are described in U.S. patent application Ser. No. 12/541,043 filed Aug. 13, 2009; U.S. application Ser. No. 12/541,050 filed Aug. 13, 2009; U.S. patent application Ser. No. 12/605,546 filed Oct. 26, 2009; U.S. patent application Ser. No. 12/605,929 filed Oct. 26, 2009 and U.S. application Ser. No. 12/944,466 filed Nov. 11, 2010. In FIGS. 5 and 6, the first polarity electrode 215 is within interior chamber 152 to contact the neutral gas flow and comprises the frame assembly 155 that is fabricated of an electrically conductive stainless steel. In another embodiment, the first polarity electrode can be any element disposed within the interior chamber 152, or extendable into interior chamber 152. The first polarity electrode 215 is electrically coupled to sleeves 115 and 170 which extends through the introducer sleeve 110 to handle 106 and conduit 136 and is connected to a first pole of the RF source energy source 130A and controller 130B. A second polarity electrode 220 is external of the internal chamber 152 and in one embodiment the electrode is spaced apart from wall 210 of the thin-wall dielectric structure 150. In one embodiment as depicted in FIGS. 5 and 6, the second polarity electrode 220 comprises a surface element of an expandable balloon member 225 carried by introducer sleeve 110. The second polarity electrode 220 is coupled by a lead (not shown) that extends through the introducer sleeve 110 and conduit 136 to a second pole of the RF source 130A. It should be appreciated that second polarity electrode 220 can be positioned on sleeve 110 or can be attached to surface portions of the expandable thin-wall dielectric structure 150, as will be described below, to provide suitable contact with body tissue to allow the electrosurgical ablation of the method of the invention. The second polarity electrode 220 can comprise a thin conductive metallic film, thin metal wires, a conductive flexible polymer or a polymeric positive temperature coefficient material. In one embodiment depicted in FIGS. 5 and 6, the expandable member 225 comprises a thin-wall compliant balloon having a length of about 1 cm to 6 cm that can be expanded to seal the cervical canal. The balloon 225 can be inflated with a gas or liquid by any inflation source 148, and can comprise a syringe mechanism controlled manually or by control unit 135. The balloon inflation source 148 is in fluid communication with an inflation lumen 228 in introducer sleeve 110 that extends to an inflation chamber of balloon 225 (see FIG. 7).

Referring back to FIG. 1, the control unit 135 can include a display 230 and touch screen or other controls 232 for setting and controlling operational parameters such as treatment time intervals, treatment algorithms, gas flows, power levels and the like. Suitable gases for use in the system include argon, other noble gases and mixtures thereof. In one embodiment, a footswitch 235 is coupled to the control unit 135 for actuating the system.

Figure 4:
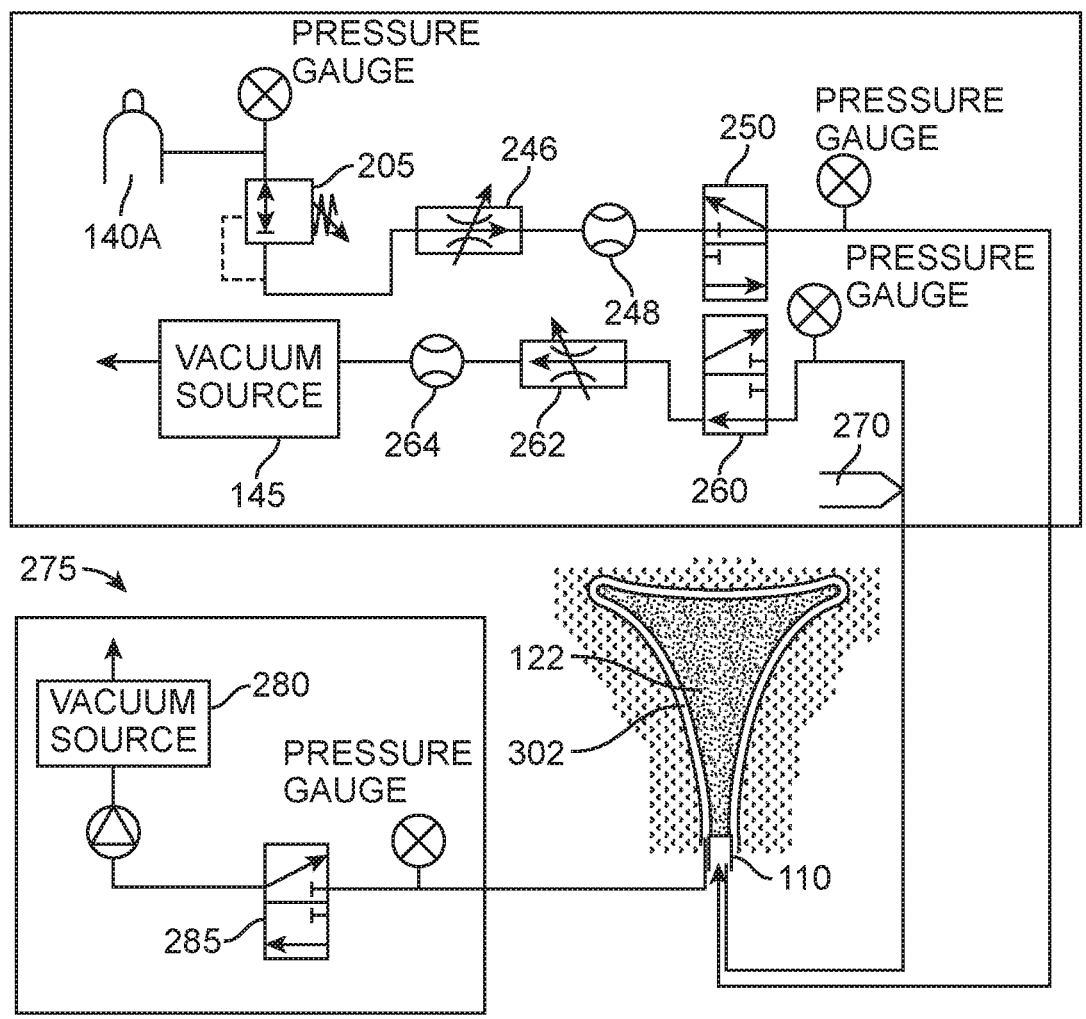
FIG. 4 is a block diagram of the gas flow components of the electrosurgical system of FIG. 1.

The box diagrams of FIGS. 3 and 4 schematically depict the system 100, subsystems and components that are configured for an endometrial ablation system. In the box diagram of FIG. 3, it can be seen that RF energy source 130A and circuitry is controlled by a controller 130B. The system can include feedback control systems that include signals relating to operating parameters of the plasma in interior chamber 152 of the dielectric structure 150. For example, feedback signals can be provided from at least one temperature sensor 240 in the interior chamber 152 of the dielectric structure 150, from a pressure sensor within, or in communication, with interior chamber 152, and/or from a gas flow rate sensor in an inflow or outflow channel of the system. FIG. 4 is a schematic block diagram of the flow control components relating to the flow of gas media through the system 100 and hand-held device 105. It can be seen that a pressurized gas source 140A is linked to a downstream pressure regulator 205, an inflow proportional valve 246, flow meter 248 and normally closed solenoid valve 250. The valve 250 is actuated by the system operator which then allows a flow of a neutral gas from gas source 140A to circulate through flexible conduit 136 and the device 105. The gas outflow side of the system includes a normally open solenoid valve 260, outflow proportional valve 262 and flow meter 264 that communicate with vacuum pump or source 145. The gas can be exhausted into the environment or into a containment system. A temperature sensor 270 (e.g., thermocouple) is shown in FIG. 4 that is configured for monitoring the temperature of outflow gases. FIG. 4 further depicts an optional subsystem 275 which comprises a vacuum source 280 and solenoid valve 285 coupled to the controller 140B for suctioning steam from a uterine cavity 302 at an exterior of the dielectric structure 150 during a treatment interval. As can be understood from FIG. 4, the flow passageway from the uterine cavity 302 can be through bore 120 in sleeve 110 (see FIGS. 2, 6 and 7) or another lumen in a wall of sleeve 110 can be provided.

FIGS. 8A-8D schematically illustrate a method of the invention wherein (i) the thin-wall dielectric structure 150 is deployed within a patient uterus and (ii) RF current is applied to a contained neutral gas volume in the interior chamber 152 to contemporaneously create a plasma 208 in the chamber and capacitively couple current through the thin dielectric wall 210 to apply ablative energy to the endometrial lining to accomplish global endometrial ablation.

Figure 8A:
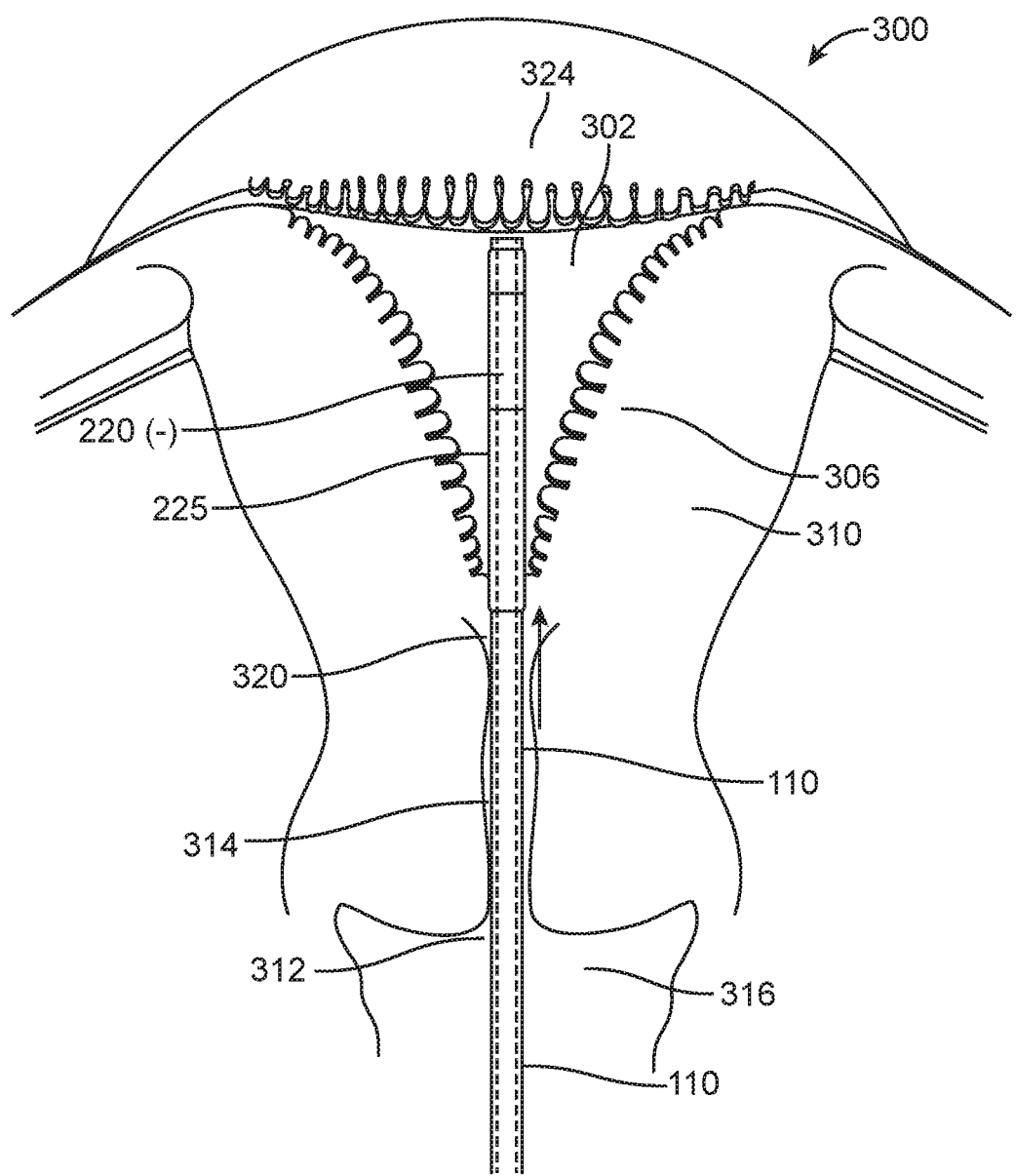
FIG. 8A is an enlarged schematic view of an aspect of a method of the invention illustrating the step introducing an introducer sleeve into a patient's uterus.

More in particular, FIG. 8A illustrates a patient uterus 300 with uterine cavity 302 surrounded by endometrium 306 and myometrium 310. The external cervical os 312 is the opening of the cervix 314 into the vagina 316. The internal os or opening 320 is a region of the cervical canal that opens to the uterine cavity 302. FIG. 8A depicts a first step of a method of the invention wherein the physician has introduced a distal portion of sleeve 110 into the uterine cavity 302. The physician gently can advance the sleeve 110 until its distal tip contacts the fundus 324 of the uterus. Prior to insertion of the device, the physician can optionally introduce a sounding instrument into the uterine cavity to determine uterine dimensions, for example from the internal os 320 to fundus 324.

Figure 8B:
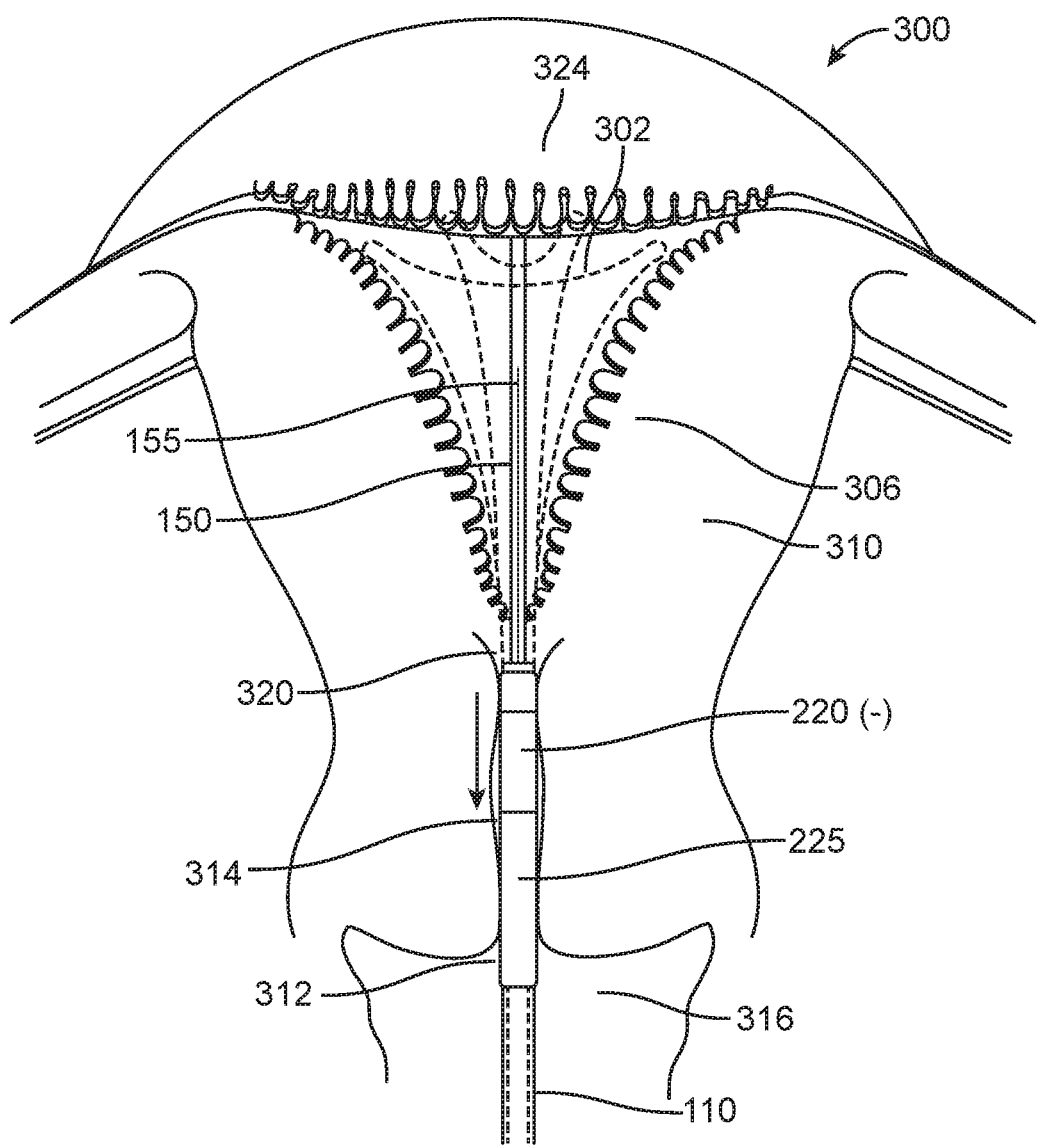
FIG. 8B is a schematic view of a subsequent step of retracting the introducer sleeve to expose a collapsed thin-wall dielectric structure and internal frame in the uterine cavity.

FIG. 8B illustrates a subsequent step of a method of the invention wherein the physician begins to actuate the first and second handle portions, 114a and 114b, and the introducer sleeve 110 retracts in the proximal direction to expose the collapsed frame 155 and thin-wall structure 150 within the uterine cavity 302. The sleeve 110 can be retracted to expose a selected axial length of thin-wall dielectric structure 150, which can be determined by markings 330 on sleeve 115 (see FIG. 1) which indicate the axial travel of sleeve 115 relative to sleeve 170 and thus directly related to the length of deployed thin-wall structure 150. FIG. 2 depicts the handle portions 114a and 114b fully approximated thus deploying the thin-wall structure to its maximum length.

In FIG. 8B, it can be understood that the spring frame elements 158a, 158b, 160a and 160b move the dielectric structure 150 from a non-expanded position to an expanded position in the uterine cavity as depicted by the profiles in dashed lines. The spring force of the frame 155 will expand the dielectric structure 150 until limited by the dimensions of the uterine cavity.

Figure 8C:
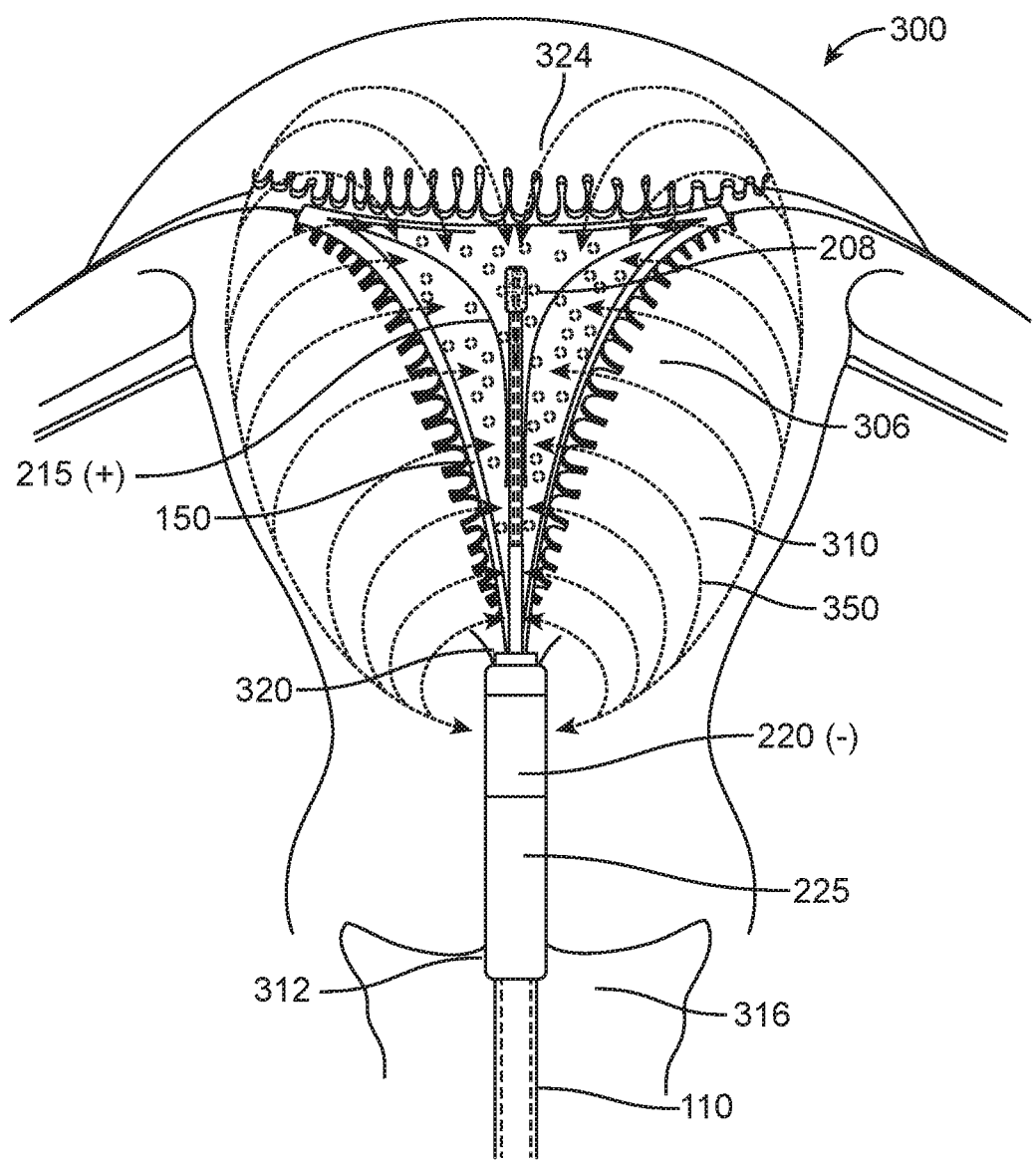
FIG. 8C is a schematic view of subsequent steps of the method, including, (i) actuating the internal frame to move the a collapsed thin-wall dielectric structure to an expanded configuration, (ii) inflating a cervical-sealing balloon carried on the introducer sleeve, and (iii) actuating gas flows and applying RF energy to contemporaneously ionize the gas in the interior chamber and cause capacitive coupling of current through the thin-wall dielectric structure to cause ohmic heating in the engaged tissue indicated by current flow paths.

FIG. 8C illustrates several subsequent steps of a method of the invention. FIG. 8C first depicts the physician continuing to actuate the first and second handle portions, 114a and 114b, which further actuates the frame 155 (see FIGS. 5-6) to expand the frame 155 and thin-wall structure 150 to a deployed triangular shape to contact the patient's endometrial lining 306. The physician can slightly rotate and move the expanding dielectric structure 150 back and forth as the structure is opened to insure it is opened to the desired extent. In performing this step, the physician can actuate handle portions, 114a and 114b, a selected degree which causes a select length of travel of sleeve 170 relative to sleeve 115 which in turn opens the frame 155 to a selected degree. The selected actuation of sleeve 170 relative to sleeve 115 also controls the length of dielectric structure deployed from sleeve 110 into the uterine cavity. Thus, the thin-wall structure 150 can be deployed in the uterine cavity with a selected length, and the spring force of the elements of frame 155 will open the structure 150 to a selected triangular shape to contact or engage the endometrium 306. In one embodiment, the expandable thin-wall structure 150 is urged toward and maintained in an open position by the spring force of elements of the frame 155. In the embodiment depicted in FIGS. 1 and 2, the handle 106 includes a locking mechanism with finger-actuated sliders 332 on either side of the handle that engage a grip-lock element against a notch in housing 333 coupled to introducer sleeve 110 (FIG. 2) to lock sleeves 115 and 170 relative to introducer sleeve 110 to maintain the thin-wall dielectric structure 150 in the selected open position.

FIG. 8C further illustrates the physician expanding the expandable balloon structure 225 from inflation source 148 to thus provide an elongated sealing member to seal the cervix 314 outward from the internal os 320. Following deployment of the thin-wall structure 150 and balloon 225 in the cervix 314, the system 100 is ready for the application of RF energy to ablate endometrial tissue 306. FIG. 8C next depicts the actuation of the system 100, for example, by actuating footswitch 235, which commences a flow of neutral gas from source 140A into the interior chamber 152 of the thin-wall dielectric structure 150. Contemporaneous with, or after a selected delay, the system's actuation delivers RF energy to the electrode arrangement which includes first polarity electrode 215 (+) of frame 155 and the second polarity electrode 220 (−) which is carried on the surface of expandable balloon member 225. The delivery of RF energy delivery will instantly convert the neutral gas in interior chamber 152 into conductive plasma 208 which in turn results in capacitive coupling of current through the dielectric wall 210 of the thin-wall structure 150 resulting in ohmic heating of the engaged tissue. FIG. 8C schematically illustrates the multiplicity of RF current paths 350 between the plasma 208 and the second polarity electrode 220 through the dielectric wall 210. By this method, it has been found that ablation depths of 3 mm to 6 mm or more can be accomplished very rapidly, for example in 60 seconds to 120 seconds dependent upon the selected voltage and other operating parameters. In operation, the voltage at which the neutral gas inflow, such as argon, becomes conductive (i.e., converted in part into a plasma) is dependent upon a number of factors controlled by the controllers 130B and 140B, including the pressure of the neutral gas, the volume of interior chamber 152, the flow rate of the gas through the chamber 152, the distance between electrode 210 and interior surfaces of the dielectric wall 210, the dielectric constant of the dielectric wall 210 and the selected voltage applied by the RF source 130, all of which can be optimized by experimentation. In one embodiment, the gas flow rate can be in the range of 5 ml/sec to 50 ml/sec. The dielectric wall 210 can comprise a silicone material having a thickness ranging from a 0.005" to 0.015 and having a relative permittivity in the range of 3 to 4. The gas can be argon supplied in a pressurized cartridge which is commercially available. Pressure in the interior chamber 152 of dielectric structure 150 can be maintained between 14 psia and 15 psia with zero or negative differential pressure between gas inflow source 140A and negative pressure or vacuum source 145. The controller is configured to maintain the pressure in interior chamber in a range that varies by less than 10% or less than 5% from a target pressure. The RF power source 130A can have a frequency of 450 to 550 KHz, and electrical power can be provided within the range of 600 Vrms to about 1200 Vrms and about 0.2 Amps to 0.4 Amps and an effective power of 40 W to 100 W. In one method, the control unit 135 can be programmed to delivery RF energy for a preselected time interval, for example, between 60 seconds and 120 seconds. One aspect of a treatment method corresponding to the invention consists of ablating endometrial tissue with RF energy to elevate endometrial tissue to a temperature greater than 45 degrees Celsius for a time interval sufficient to ablate tissue to a depth of at least 1 mm. Another aspect of the method of endometrial ablation of consists of applying radiofrequency energy to elevate endometrial tissue to a temperature greater than 45 degrees Celsius without damaging the myometrium.

Figure 8D:
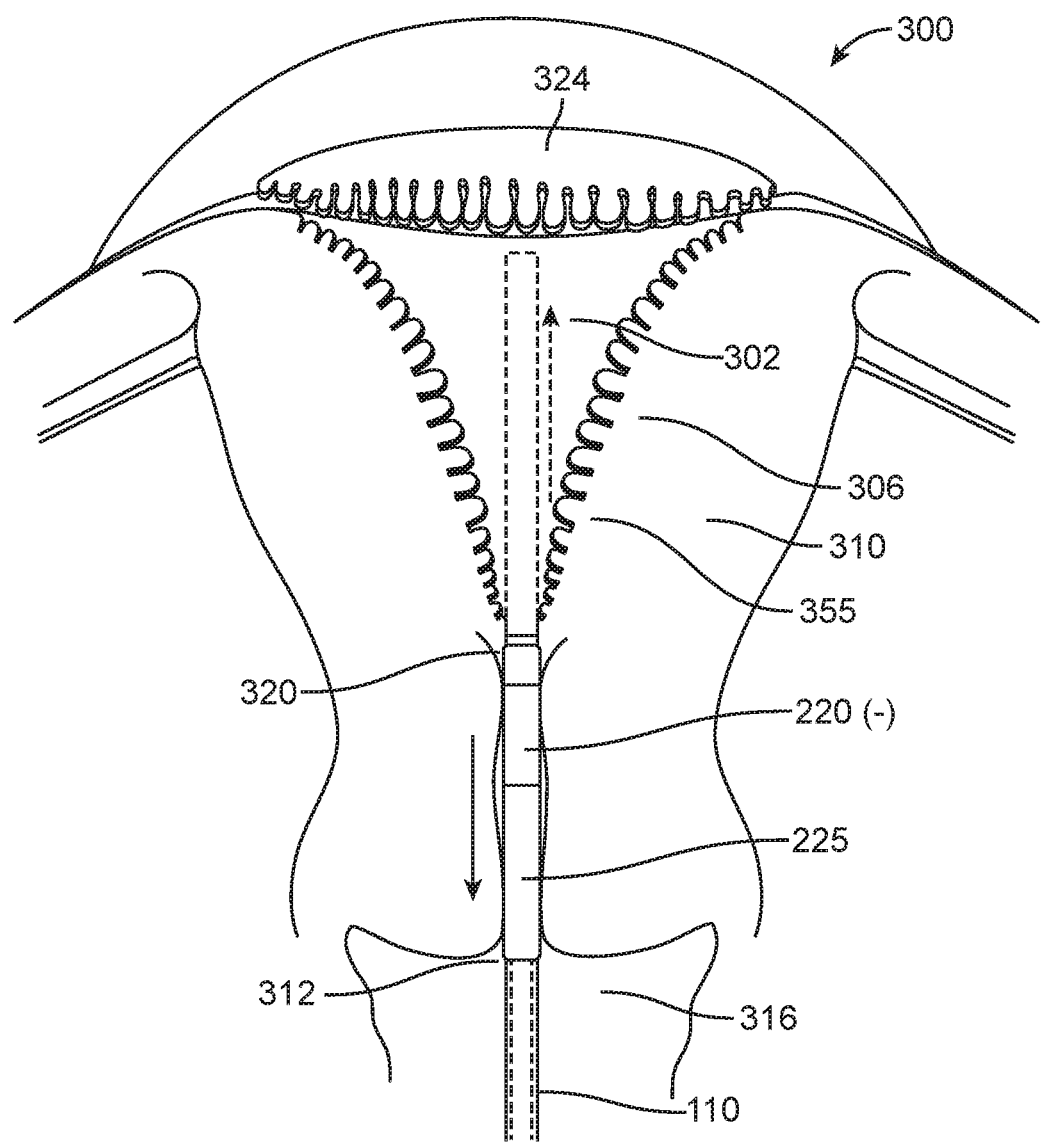
FIG. 8D is a schematic view of a subsequent steps of the method, including: (i) advancing the introducer sleeve over the thin-wall dielectric structure to collapse it into an interior bore shown in phantom view, and (ii) withdrawing the introducer sleeve and dielectric structure from the uterine cavity.

FIG. 8D illustrates a final step of the method wherein the physician deflates the expandable balloon member 225 and then extends sleeve 110 distally by actuating the handles 114a and 114b to collapse frame 155 and then retracting the assembly from the uterine cavity 302. Alternatively, the deployed working end 122 as shown in FIG. 8C can be withdrawn in the proximal direction from the uterine cavity wherein the frame 155 and thin-wall structure 150 will collapse as it is pulled through the cervix. FIG. 8D shows the completed ablation with the ablated endometrial tissue indicated at 360.

In another embodiment, the system can include an electrode arrangement in the handle 106 or within the gas inflow channel to pre-ionize the neutral gas flow before it reaches the interior chamber 152. For example, the gas inflow channel can be configured with axially or radially spaced apart opposing polarity electrodes configured to ionize the gas inflow. Such electrodes would be connected in separate circuitry to an RF source. The first and second electrodes 215 (+) and 220 (−) described above would operate as described above to provide the current that is capacitively coupled to tissue through the walls of the dielectric structure 150. In all other respects, the system and method would function as described above.

Figure 9:
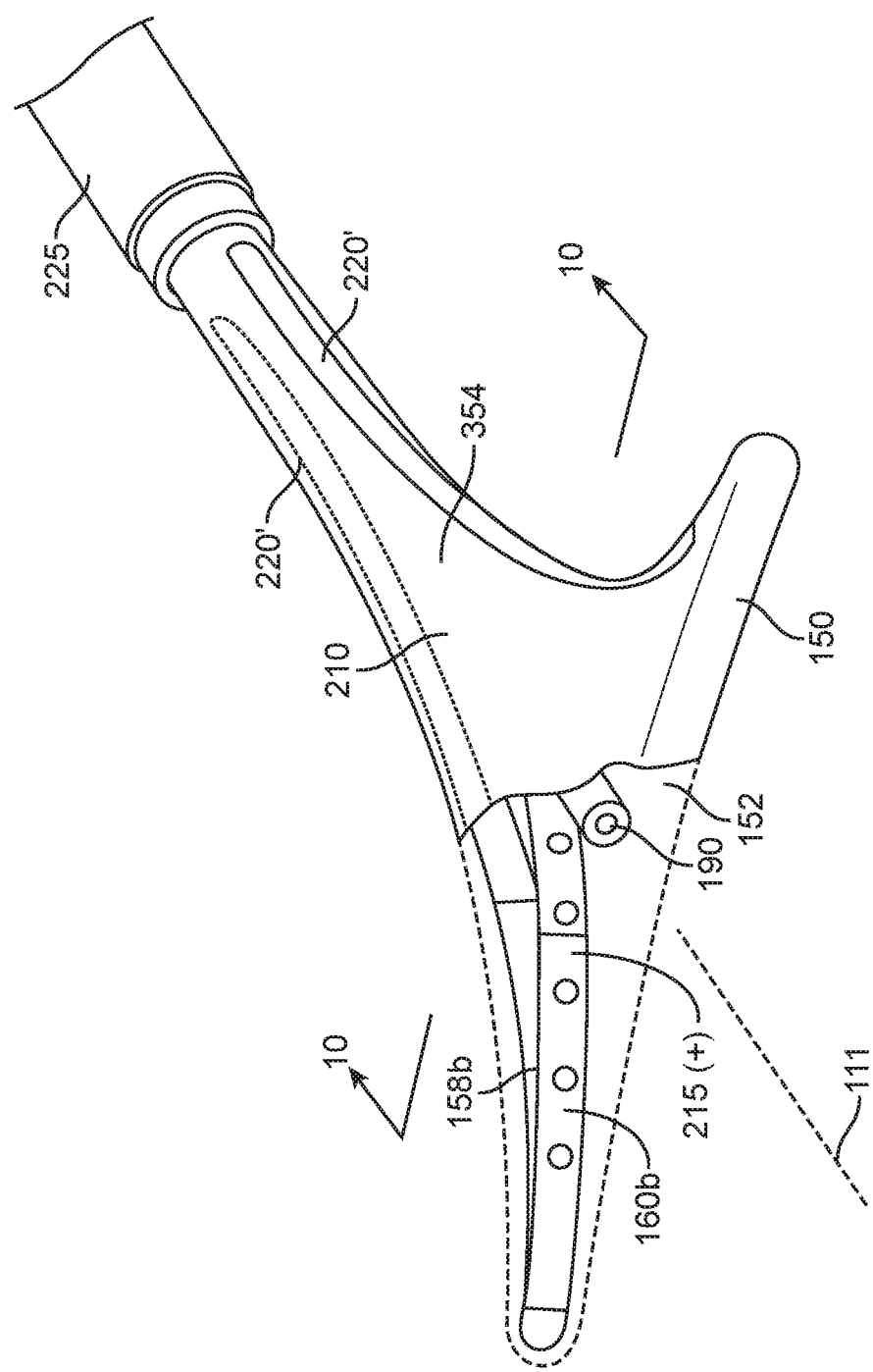
FIG. 9 is a cut-away perspective view of an alternative expanded thin-wall dielectric structure similar to that of FIGS. 5 and 6 show an alternative electrode configuration.
Figure 10:
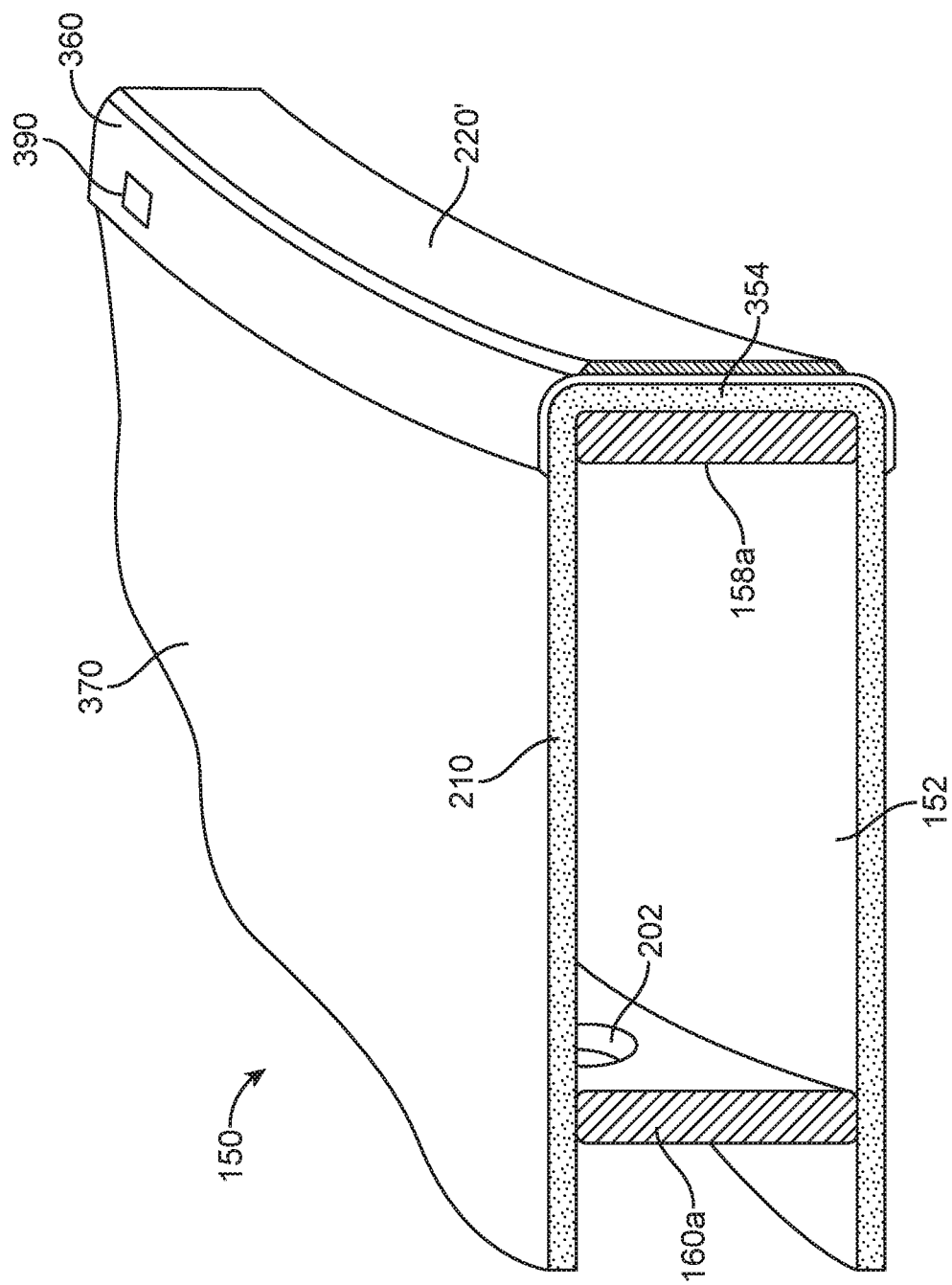
FIG. 10 is an enlarged cut-away view of a portion of the expanded thin-wall dielectric structure of FIG. 9 showing the electrode configuration.

Now turning to FIGS. 9 and 10, an alternate working end 122 with thin-wall dielectric structure 150 is shown. In this embodiment, the thin-wall dielectric structure 150 is similar to that of FIGS. 5 and 6 except that the second polarity electrode 220' that is exterior of the internal chamber 152 is disposed on a surface portion 370 of the thin-wall dielectric structure 150. In this embodiment, the second polarity electrode 220' comprises a thin-film conductive material, such as gold, that is bonded to the exterior of thin-wall material 210 along two lateral sides 354 of dielectric structure 150. It should be appreciated that the second polarity electrode can comprise one or more conductive elements disposed on the exterior of wall material 210, and can extend axially, or transversely to axis 111 and can be singular or multiple elements. In one embodiment shown in more detail in FIG. 10, the second polarity electrode 220' can be fixed on another lubricious layer 360, such as a polyimide film, for example KAPTON®. The polyimide tape extends about the lateral sides 354 of the dielectric structure 150 and provides protection to the wall 210 when it is advanced from or withdrawn into bore 120 in sleeve 110. In operation, the RF delivery method using the embodiment of FIGS. 9 and 10 is the same as described above, with RF current being capacitively coupled from the plasma 208 through the wall 210 and endometrial tissue to the second polarity electrode 220' to cause the ablation.

FIG. 9 further shows an optional temperature sensor 390, such as a thermocouple, carried at an exterior of the dielectric structure 150. In one method of use, the control unit 135 can acquire temperature feedback signals from at least one temperature sensor 390 to modulate or terminate RF energy delivery, or to modulate gas flows within the system. In a related method of the invention, the control unit 135 can acquire temperature feedback signals from temperature sensor 240 in interior chamber 152 (FIG. 6 to modulate or terminate RF energy delivery or to modulate gas flows within the system.

Figure 11:
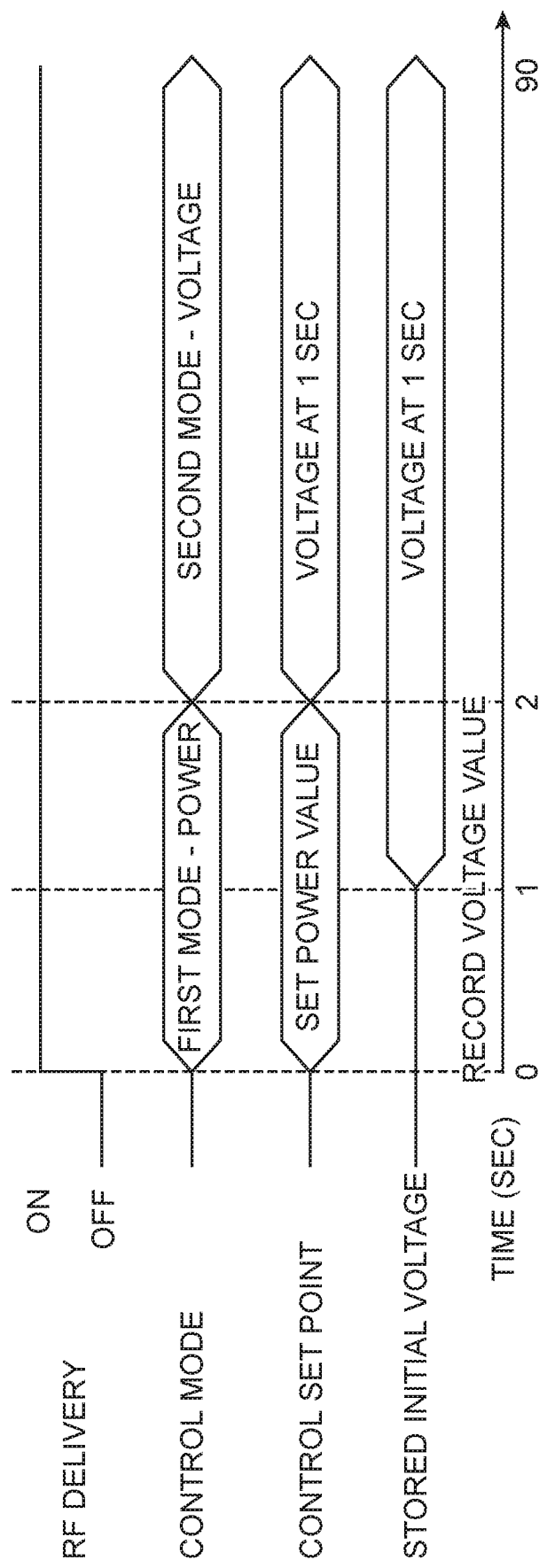
FIG. 11 is a diagram of a radiofrequency energy delivery apparatus and method corresponding to the invention.

In another aspect of the invention, FIG. 11 is a graphic representation of an algorithm utilized by the RF source 130A and RF controller 130B of the system to controllably apply RF energy in an endometrial ablation procedure. In using the expandable dielectric structure 150 of the invention to apply RF energy in an endometrial ablation procedure as described above, the system is configured to allow the dielectric structure 150 to open to different expanded dimensions depending on the size and shape of the uterine cavity 302. The axial length of dielectric structure 150 also can be adjusted to have a predetermined axial length extended outward from the introducer sleeve 110 to match a measured length of a uterine cavity. In any case, the actual surface area of the expanded dielectric structure 150 within different uterine cavities will differ—and it would be optimal to vary total applied energy to correspond to the differing size uterine cavities.

FIG. 11 represents a method of the invention that automatically determines relevant parameters of the tissue and the size of uterine cavity 302 to allow for selection of an energy delivery mode that is well suited to control the total applied energy in an ablation procedure. In embodiments, RF energy is applied at constant power for a first time increment, and the following electrical parameters (e.g., voltage, current, power, impedance) are measured during the application of energy during that first time increment. The measured electrical parameters are then used (principally, power and current, V=P/I) to determine a constant voltage to apply to the system for a second time interval. The initial impedance may be also be utilized by the controller as a shutoff criteria for the second treatment interval after a selected increase in impedance.

For example, in FIG. 11, it can be seen that a first step following the positioning of the dielectric structure in the uterine cavity 302 is to apply radiofrequency energy in a first mode of predetermined constant power, or constant RF energy ("FIRST MODE–POWER"). This first power is sufficient to capacitively couple current across the dielectric to contacted tissue, wherein empirical studies have shown the power can be in the range of 50 W-300 W, and in one embodiment is 80 W. This first power mode is applied for a predetermined interval which can be less than 15 seconds, 10 seconds, or 5 seconds, as examples, and is depicted in FIG. 11 as being 2 seconds. FIG. 11 shows that, in accordance with embodiments, the voltage value is determined a voltage sensor in controller 130A and is recorded at the "one-second" time point after the initiation of RF energy delivery. The controller includes a power sensor, voltage sensor and current sensor as is known in the art. This voltage value, or another electrical parameter, may be determined and recorded at any point during the interval, and more than one recording may be made, with averages taken for the multiple recordings, or the multiple recordings may be used in another way to consistently take a measurement of an electrical value or values. FIG. 11 next illustrates that the controller algorithm switches to a second mode ("SECOND MODE–VOLTAGE") of applying radiofrequency energy at a selected constant voltage, with the selected constant voltage related to the recorded voltage (or other electrical parameter) at the "one-second" time point. In one embodiment, the selected constant voltage is equal to the recorded voltage, but other algorithms can select a constant voltage that is greater or lesser than the recorded voltage but determined by a factor or algorithm applied to the recorded voltage. As further shown in FIG. 11, the algorithm then applies RF energy over a treatment interval to ablate endometrial tissue. During this period, the RF energy is varied as the measured voltage is kept constant. The treatment interval can have an automatic time-out after a predetermined interval of less that 360 seconds, 240 seconds, 180 seconds, 120 seconds or 90 seconds, as examples.

By using the initial delivery of RF energy through the dielectric structure 150 and contacted tissue in the first, initial constant power mode, a voltage level is recorded (e.g., in the example, at one second) that directly relates to a combination of (i) the surface area of the dielectric structure, and the degree to which wall portions of the dielectric structure have been elastically stretched; (ii) the flow rate of neutral gas through the dielectric structure and (iii) the impedance of the contacted tissue. By then selecting a constant voltage for the second, constant voltage mode that is directly related to the recorded voltage from the first time interval, the length of the second, treatment interval can be the same for all different dimension uterine cavities and will result in substantially the same ablation depth, since the constant voltage maintained during the second interval will result in power that drifts off to lower levels toward the end of the treatment interval as tissue impedance increases. As described above, the controller 130A also can use an impedance level or a selected increase in impedance to terminate the treatment interval.

The algorithm above provides a recorded voltage at set time point in the first mode of RF energy application, but another embodiment can utilize a recorded voltage parameter that can be an average voltage over a measuring interval or the like. Also, the constant voltage in the second mode of RF energy application can include any ramp-up or ramp-down in voltage based on the recorded voltage parameter.

In general, an electrosurgical method for endometrial ablation comprises positioning a RF ablation device in contact with endometrial tissue, applying radiofrequency energy in a first mode based on a predetermined constant power over a first interval, and applying radiofrequency energy in a second mode over a second interval to ablate endometrial tissue wherein the energy level of the second mode being based on treatment voltage parameters obtained or measured during the first interval. Power during the first interval is constant and power during the second period is varied to maintain voltage at a constant level. Another step in applying RF energy in the first mode includes the step of recording a voltage parameter in the first interval, wherein the voltage parameter is at least one of voltage at a point in time, average voltage over a time interval, and a change or rate of change of voltage. The second mode includes setting the treatment voltage parameters in relation to the voltage parameter recorded in the first interval.

Referring to FIG. 11, it can be understood that an electrosurgical system for endometrial ablation comprises a radiofrequency ablation device coupled to an radiofrequency power supply, and control means connected to the radiofrequency power supply for switching the application of radiofrequency energy between a constant power mode and a constant voltage mode. The control means includes an algorithm that (i) applies radiofrequency energy in the first mode (ii) records the voltage within a predetermined interval of the first mode, and (iii) applies radiofrequency energy in the second mode with constant voltage related to the recorded voltage.

In another aspect, the invention comprises a radiofrequency power supply, a means for coupling the radiofrequency power supply to an ablation device configured for positioning in a uterine cavity, the ablation device comprising a dielectric for contacting endometrial tissue, a system for recording an electrical parameter of the ablation device and contacted tissue, and a feedback system for varying the application of radiofrequency energy to tissue between a constant power mode and a constant voltage mode based on a recorded electrical parameter.

Figure 12:
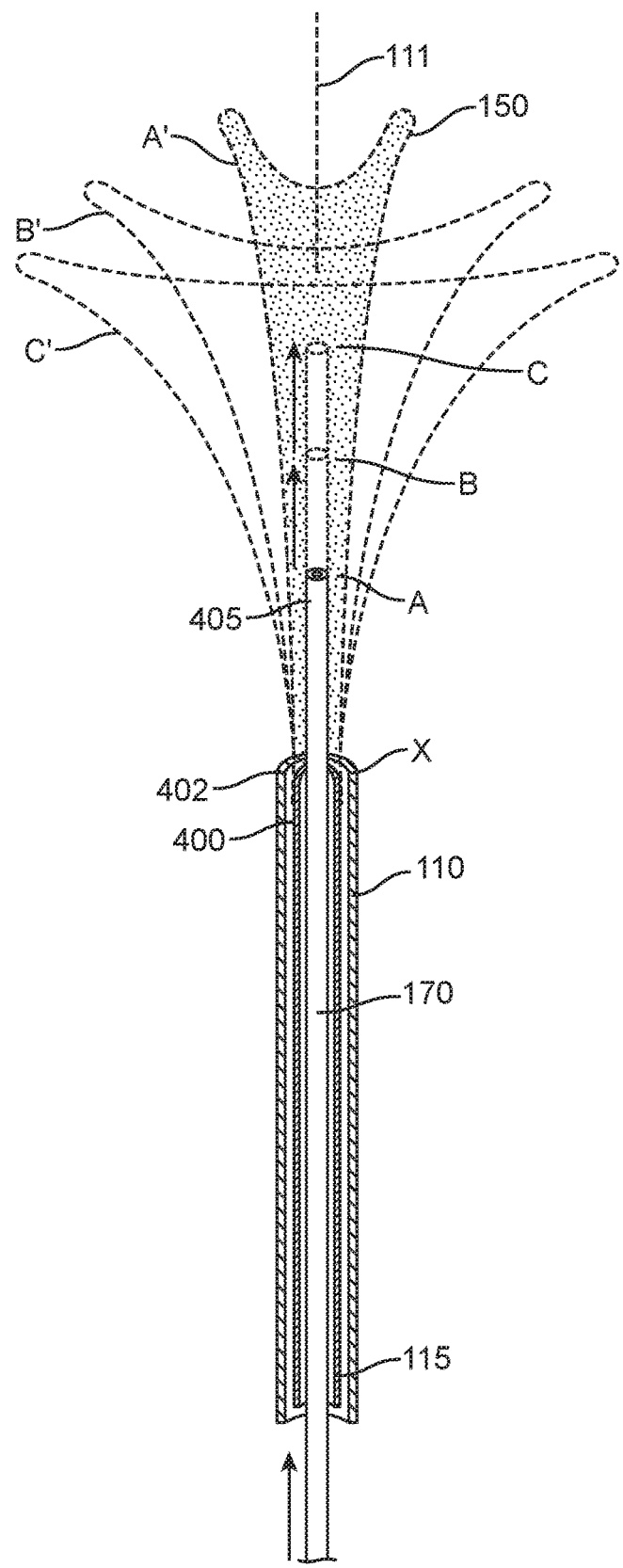
FIG. 12 is a schematic view of the working end of the ablation device of FIGS. 1-2 depicting three outlines of the expandable working end in a range of slightly-expanded to fully-expanded positions.
Figure 13A:
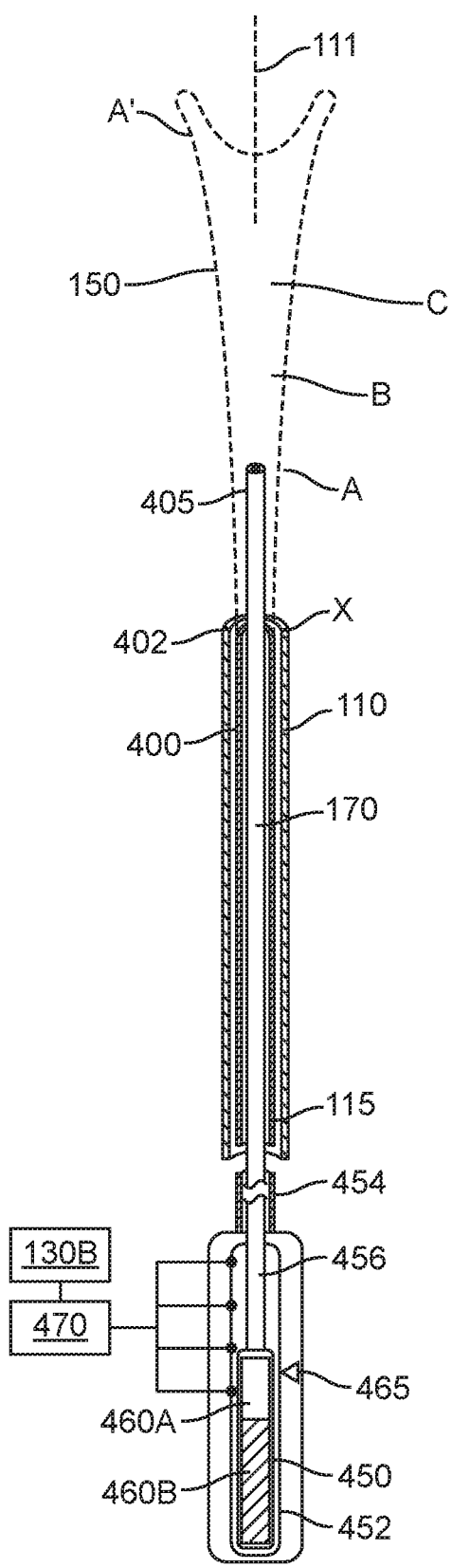
FIG. 13A is a schematic representation of an indicator mechanism in the handle of the ablation device of FIGS. 1-2 for indicating a first degree of expansion of the dielectric structure in a range shown in FIG. 12.
Figure 13B:
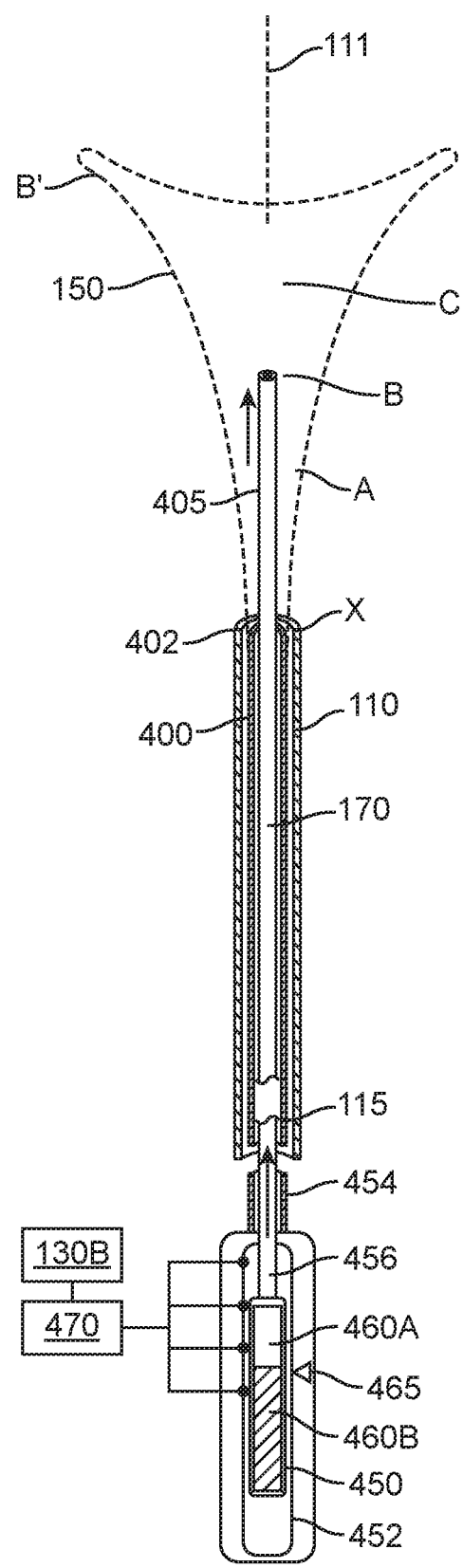
FIG. 13B is a schematic representation of the indicator mechanism of FIG. 13A indicating a second the degree of expansion of the dielectric structure.

In another embodiment of the invention, FIGS. 12, 13A and 13B depict components of the ablation device of FIGS. 1-2 that provide the physician with an indication of the degree to which the dielectric structure 150 has opened in the patient's uterine cavity 302. It can be understood from FIGS. 5, 6 and 8C that the spring frame 155 that moves the dielectric structure 150 from a contracted, linear shape (FIG. 8B) to an expanded, triangular shape (FIG. 8C) results from actuating the handle 106 to move the assembly of inner sleeve 170, intermediate sleeve 115, frame 155 and dielectric structure 150 distally relative to the introducer sleeve 110 to thus expose and deploy the dielectric structure 150 in the uterine cavity 302.

Referring to FIG. 12, it can be seen that inner sleeve 170 and intermediate sleeve 115 are shown for convenience without their respective welded connections to spring frame elements 158a, 158b, 160a and 160b. The frame elements 158a, 158b, 160a and 160b and their springing function can be seen in FIGS. 5 and 6. In FIG. 12, the introducer sheath 110 is shown as being moved proximally relative to the dielectric structure 150 which corresponds to a position of the dielectric structure 150 shown in FIG. 8B. In the schematic view of FIG. 12, the distal end 400 of sleeve 170 has an axial position X and can be approximately the same axial position as the distal end 402 of the introducer sleeve 110. It can be understood that when the dielectric structure 150 and interior spring frame 155 are deployed in a uterine cavity, the spring force of frame 155 will tend to open the dielectric structure 150 from a position in FIG. 8B toward the position of FIG. 8C. In FIG. 12, an initial position of the distal end 405 of sleeve 170 has an axial position indicated at A which corresponds to plan shape A' of the dielectric structure 150. In a typical procedure, the spring force of frame 155 will move the distal end 405 of sleeve 170 toward an axial position B which corresponds to expanded dielectric plan shape B' or toward an axial position C and corresponding expanded dielectric plan shape C'. Dielectric plan shape C' represents a fully expanded dielectric structure 150. In order to allow the spring force of frame 155 to expand the frame and dielectric structure 150, the physician may gently and very slightly rotate, tilt and translate the expanding dielectric structure 150 in the uterine cavity 302. After thus deploying the dielectric structure, the different dimensions of uterine cavities will impinge on the degree of expansion of the dielectric structure 150—and the size and surface area of the dielectric structure, as an example, will be within the dimension range between plan shape A' and plan shape C' of FIG. 12.

In one aspect of the invention, it is important for the system and physician to understand the degree to which the dielectric structure 150 and frame 155 has expanded in the uterine cavity. If the dielectric structure 155 has not expanded to a significant degree, it may indicate that the uterine cavity is very small or very narrow, that fibroids are impinging on dielectric structure preventing its expansion, that the uterine cavity is very asymmetric, or that a tip of the dielectric structure and frame 155 has penetrated into an endometrial layer, perforated the uterine wall or followed a dissection path created by a sounding procedure just prior to deployment of the dielectric structure. Further, in one system embodiment, the dielectric structure 150 is preferred to have a minimum surface area directly related to its expanded shape to thus cooperate with an RF energy delivery algorithm.

In one embodiment, the system provides a "degree of frame-open" signaling mechanism for signaling the physician that the frame 155 and dielectric structure 150 has expanded to a minimum predetermined configuration. The signaling mechanism is based on the relative axial location of inner sleeve 170 and sleeve 115 as can be understood from FIGS. 12 and 13A-13B. In FIGS. 1 and 2, it can be seen that a sliding element 450 is exposed in a top portion of handle component 114B to slide axially in a slot 452. In a schematic view of handle component 114b in FIGS. 13A-13B, it can be seen that the proximal end 454 of sleeve 115 is fixed in handle component 114b. Further, the proximal end of 456 of the inner sleeve 170 is connected to the sliding element 450 that slides in slot 452. Thus, it can be understood that inner sleeve 170 is slidable and free-floating in the bore 175 of sleeve 115 and can be moved axially to and fro depending to the opening spring force of frame 155—which force can be constrained by the frame being withdrawn into the bore 120 of introducer sleeve 110 or by uterine walls impinging on the dielectric structure 150 and frame 155 when deployed in a uterine cavity. As can be seen in FIGS. 1, 2, 13A and 13B, the sliding element has at least two axially-extending indicators 460A and 460B that can be different colors that slide axially relative to status-indicating arrow element 465 in a fixed location in the handle 114b. In one embodiment, indicator 460A can be red for "stop" and indicator 460B can be "green", for indicating whether to stop proceeding with the procedure, or to go ahead with the ablation procedure. In FIG. 13A, it can be seen that inner sleeve 170 and its distal end 405 are only axially extended at point A which corresponds to dielectric expansion profile A'. The limited expansion of dielectric structure at profile A' is indicated at the slider 450 wherein the arrow 465 points to the red 'stop" indicator 460A which indicates to the physician to stop and not proceed with the ablation procedure due to limited expansion of dielectric structure 150.

FIG. 13B depicts an extension of inner sleeve 170 and its distal end 405 to axially extended at point B which corresponds to dielectric expansion profile B'. This intermediate expansion of dielectric structure 150 at profile B' is indicated to the physician by observing slider 450 wherein arrow 465 points to the green indicator 460B which indicates "go"— that is, the physician can proceed with the ablation procedure since the dielectric structure 150 and frame 155 have expanded to a predetermined degree that cooperates with an RF energy delivery algorithm. It can be understood from FIG. 13B that sleeve 170 can move axially toward extended position C with corresponding dielectric structure profile C' and indicator arrow 465 will again point to the "go" portion 460B of sliding element which is green.

In another aspect of the invention also depicted in FIGS. 13A-13B, the handle component 114b can include a electrical contact sensor 470 that detects the axial movement of sliding element 450 and sleeve 170 relative to sleeve 115 to thereby provide an electronic signal indicating the degree of expansion of the frame 155 and dielectric structure 150. In one embodiment, the electronic signal communicates with RF controller 130B to disable the system if the relative axial positions of sleeves 170 and 115 do not indicate a predetermined degree of expansion of the frame 155 and dielectric structure. The system can further include an override mechanism, whereby the physician can manipulate the instrument slightly back and forth and rotationally to evaluate whether the frame 155 opens incrementally more. In another embodiment, the electrical sensor 470 can detect a plurality of degrees of expansion of the frame 155 and dielectric structure 150, for example as depicted by an electrical contact be activated at positions AA, BB, CC, and DD of the slider 450 in FIGS. 13A-13B, wherein each degree of expansion of frame 155 signals the controller to select a different RF delivery algorithm. The various different RF delivery algorithms can alter at least one of: (i) the duration of a treatment interval, for example from between 60 seconds and 240 seconds, (ii) the relation between a recorded voltage and a treatment voltage as described in the text accompanying FIG. 11 above (e.g., the treatment voltage can equal the recorded voltage, or vary as a factor about 0.8, 0.9, 1.0, 1.1 or 1.2 times the recorded voltage; (iv) can vary a ramp-up or ramp-down in voltage, or can a time interval of the first and second modes of RF energy delivery described above. The number of degrees of expansion of frame 155 and dielectric structure can range from 1 to 10 or more.

The embodiment of FIGS. 1, 2, 13A and 13B depict indicator subsystems that include visual and electrical signals, but it should be appreciated that the indicator subsystem can provide any single or combination signals that can be visual, aural or tactile with respect to the operator and/or electrically communicate with microprocessors, programmable logic devices or controllers of the ablation system.

Figure 14A:
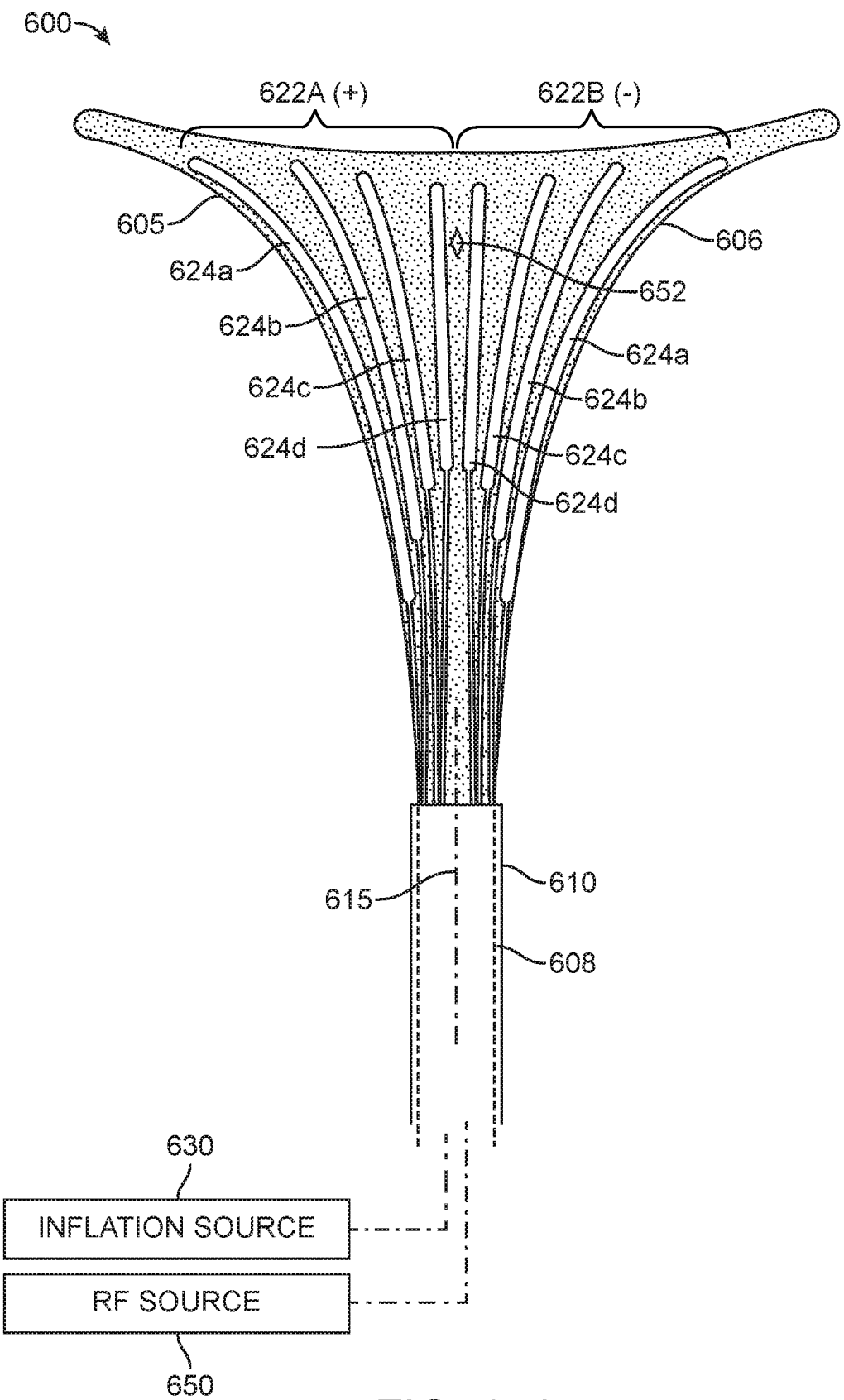
FIG. 14A is a schematic view of another embodiment of an expandable working end that is frame-expandable and carries a bi-polar electrode arrangement.
Figure 14B:
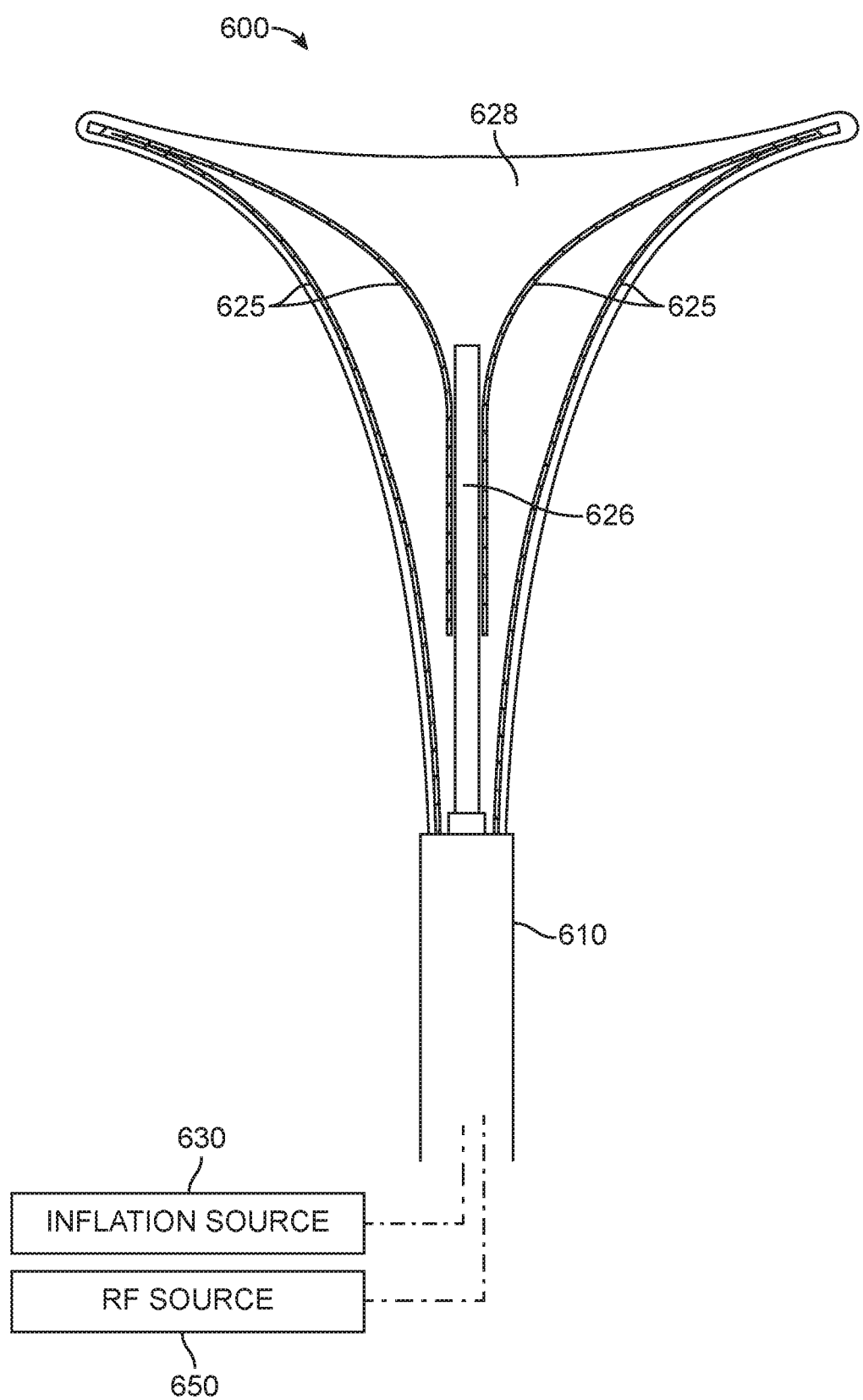
FIG. 14B is a cut-away view of the expandable working end of FIG. 14A showing the expandable frame.

FIGS. 14A-14B schematically illustrate another embodiment of an electrosurgical working end 600 that comprises a thin-wall, complaint elastomeric member 605 having an energy-delivery surface 606 that is capable of substantially conforming to the surface of a patient's uterine cavity. The working end 600 is shown in an expanded configuration and can be contracted to be withdrawn into bore 608 in introducer sleeve 610 extending along axis 615. In this embodiment, the energy-delivery surface 606 carries at least one RF electrode coupled to a radiofrequency generator 650. In the embodiment of FIG. 14A, the electrode's arrangement includes bi-polar electrodes consisting of first polarity electrode 622A and second polarity electrode 622B, for example with electrode elements 624*a*-624*d* in branches to allow lateral expansion of the elastomeric member. The opposing side of the energy-delivery surface 606 can have mirror image electrodes so that the bi-polar electrodes are carried in four quadrants, however the number of electrodes can range from 2 to 100 or more and operate with or without multiplexing to apply energy to engaged tissue.

As shown in the schematic view of FIG. 15, the bi-polar electrode assembly 622A is embedded in the elastomeric wall, such as a silicone wall. FIG. 15 illustrates an electrode foil 640 that is bonded to a polymer backing tape 642 (e.g., Kapton® or the like) and then molded into a balloon wall 644. The electrode foil 640 and backing tape 642 can be acquired from a flex-circuit manufacturer, such as All Flex, 1705 Cannon Lane, Northfield, Minn. 55057. The electrodes are coupled to RF source 650 and controller by electrical leads extending through sleeve 610 (FIG. 14A).

As shown in transparent view of FIG. 14B, the electrosurgical working end 600 of FIG. 14A can be expanded by a translatable sleeve 626 and triangular frame 625 as described in previous embodiments. The frame 625 supports the electrosurgical working end 600 in an open configuration, with at least the outer portion 628 of complaint elastomeric member 605 of the electrosurgical working end 600 being inflatable to engage with a patient's uterine cavity.

Referring to FIG. 14A, the expandable member 605 can carry at least one thermocouple 652 that is connected to a controller for modulating electrical current to the electrode arrangement. By this means, the engaged tissue can be maintained at or about a targeted temperature, for example ranging between about 80° C. and 200° C.

Figure 16:
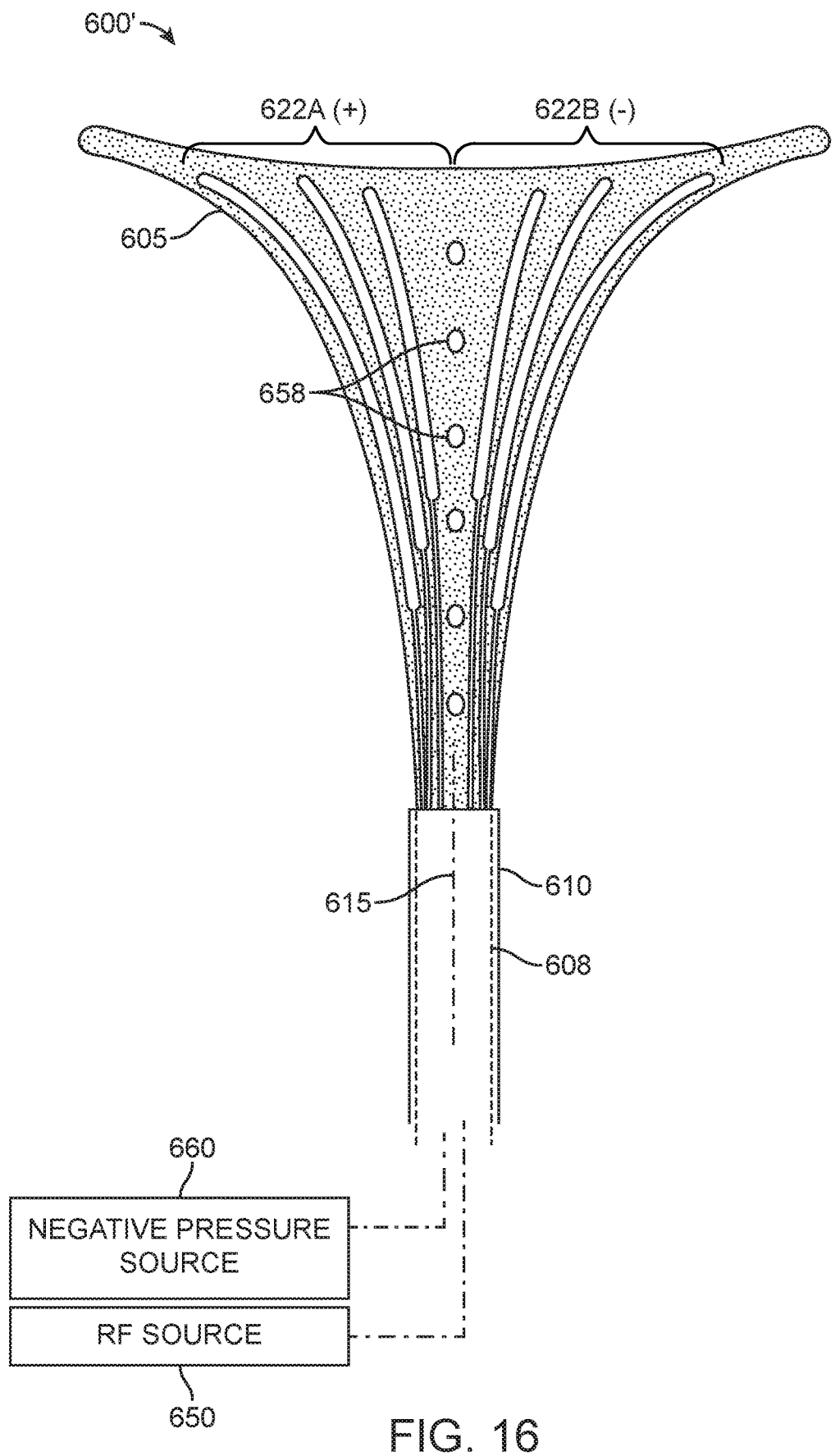
FIG. 16 is a schematic view of an alternative frame-expandable working end that includes apertures in the surface in communication with a negative pressure source.

FIG. 16 shows a schematic view of another working end 600' similar to that of FIGS. 14A-14B except that the thin-wall elastomeric structure 605 is not configured with an inflatable interior chamber. The embodiment of FIG. 16 has a surface with at least one aperture 658 therein for permitting a negative pressure source 660 to be in communication with the uterine cavity through the apertures 658. By this means, steam can be evacuated through the energy delivery surface 605 into the interior of frame 625 that holds the working end open. The steam, water droplets, etc. can be evacuated through a lumen in the introducer 610.

Figure 17:
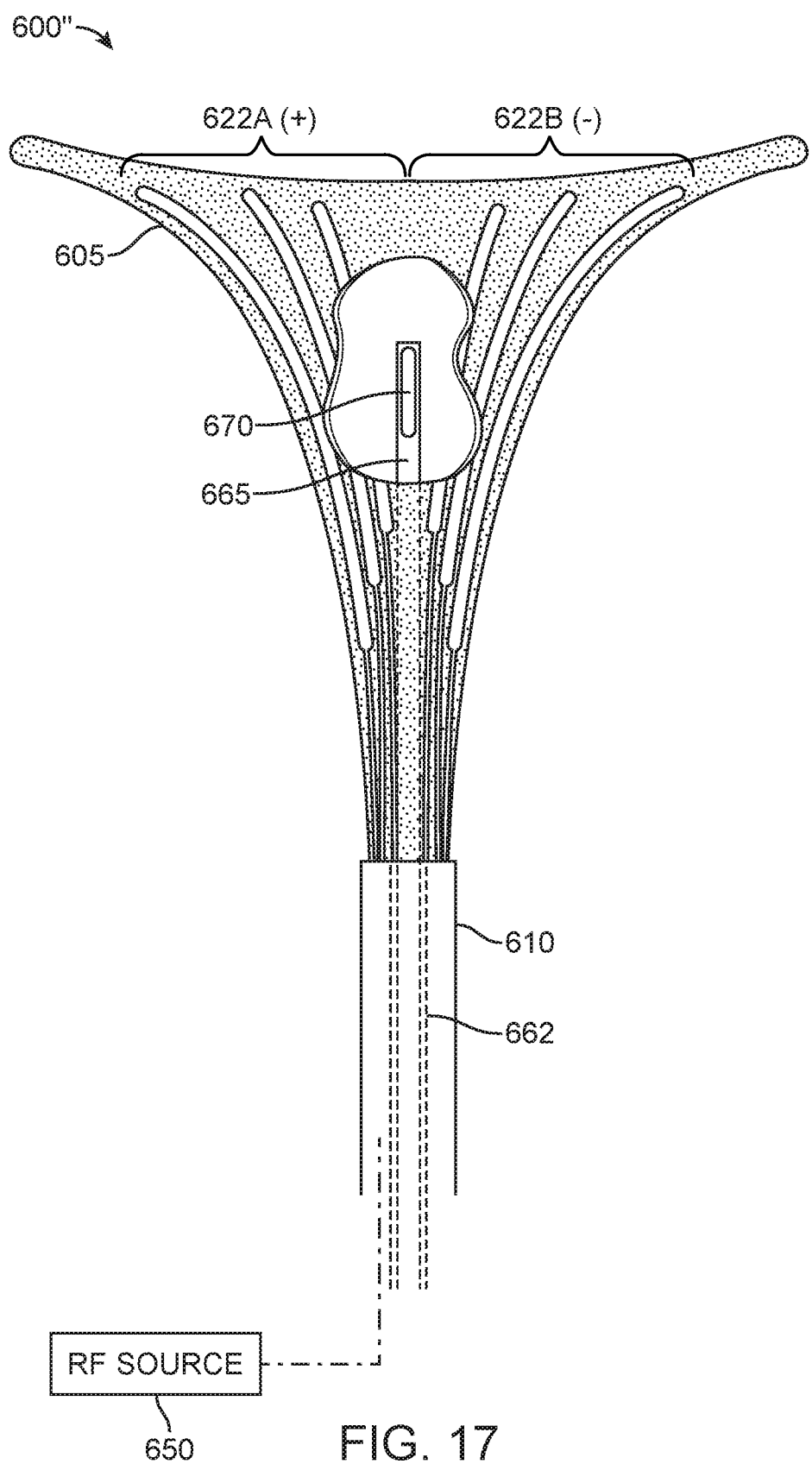
FIG. 17 is a schematic view of an alternative frame-expandable working end that includes apertures in the surface in communication with a negative pressure source.

FIG. 17 is a schematic view of another working end 600" similar to that of FIG. 14A or FIG. 16 further configured with a channel 662 in the introducer that can accommodate an elongate member 665 that carries distal ultrasound transducer mechanism indicated at 670. The ultrasound transducer 670 allows the physician to monitor the depth of ablation in real time during an endometrial ablation procedure. In this embodiment, the ultrasound transducer 670 is re-usable and is mounted on a non-disposable tool. In another embodiment (not shown), the ultrasound transducer 670 can be disposable and carried within the working end.

Figure 18:
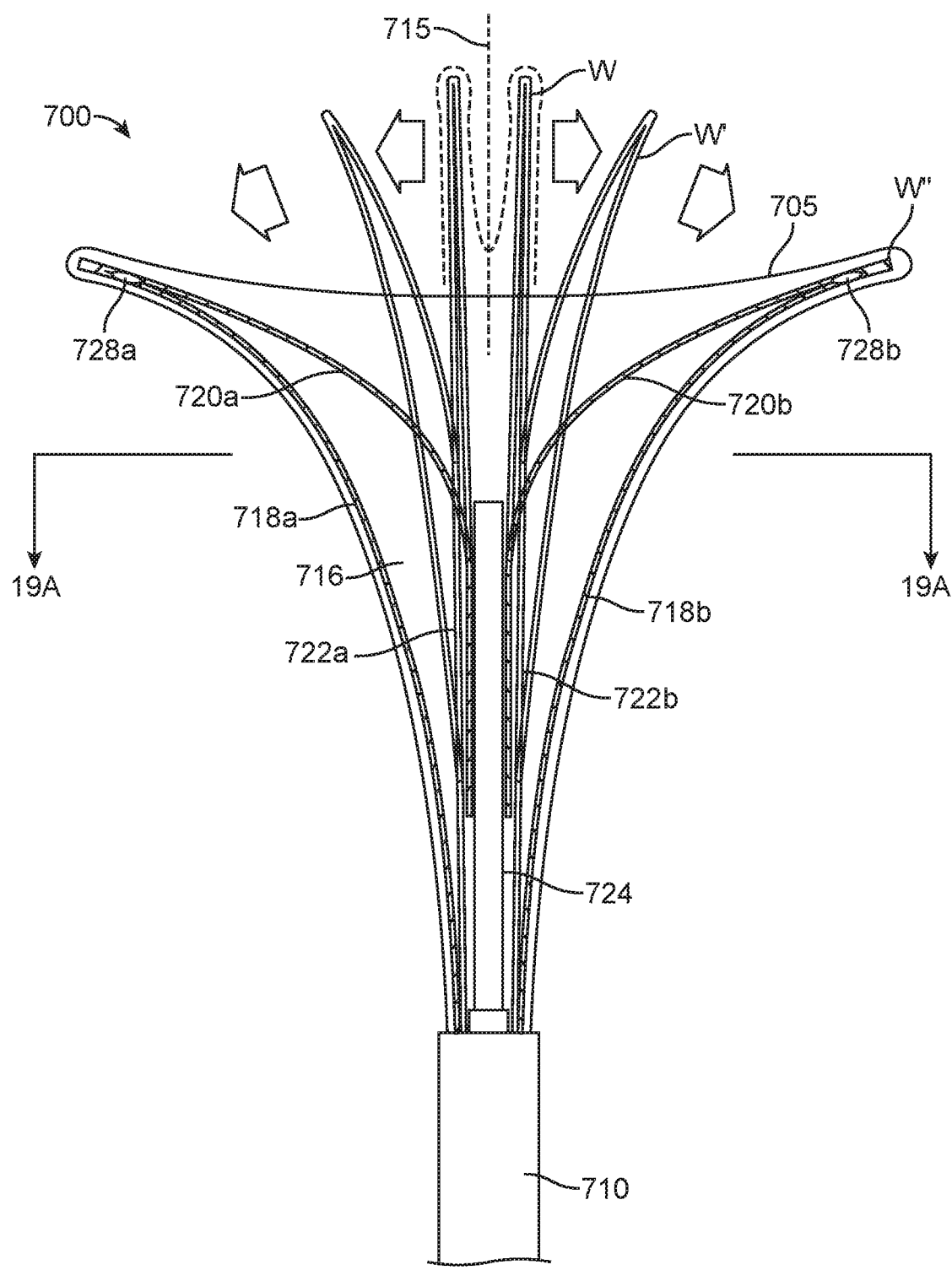
FIG. 18 illustrates another embodiment of a working end in accordance with the principles of the present invention.
Figure 19A:
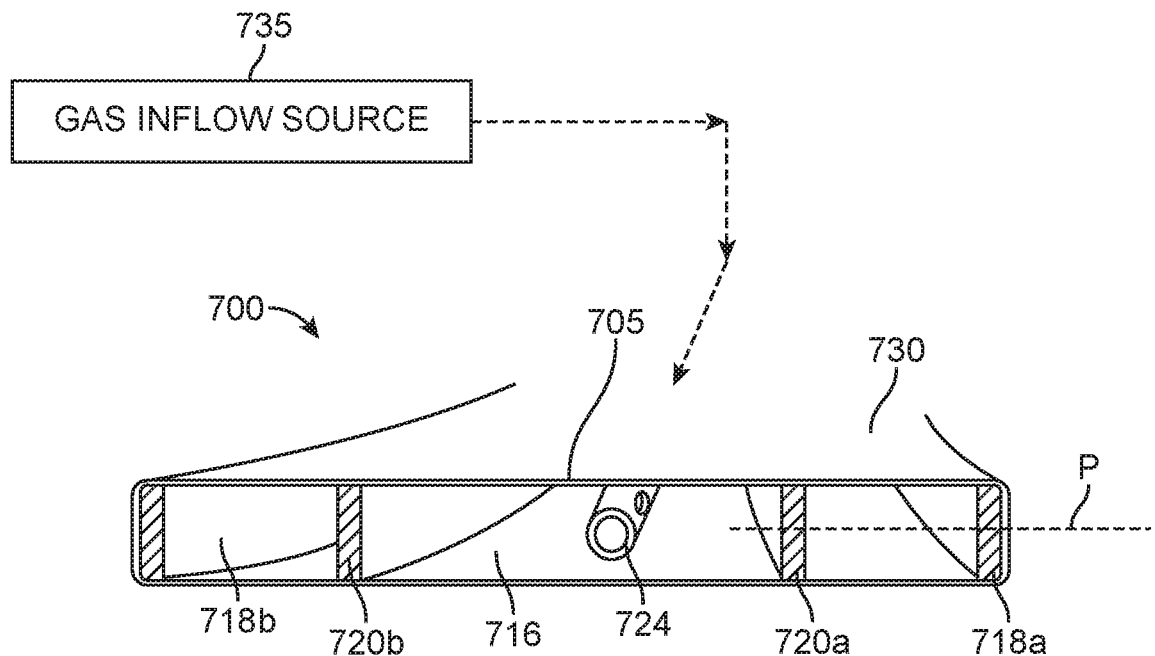
FIG. 19A is a sectional view of the working end of FIG. 18 taken along line 19A-19A with the dielectric membrane expanded in lateral directions by the interior frame.
Figure 19B:
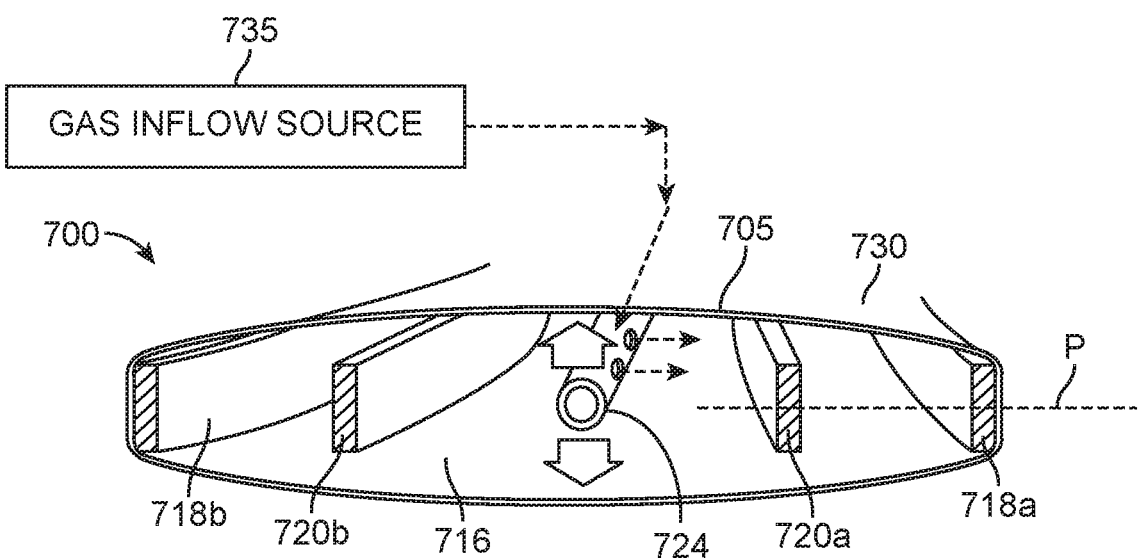
FIG. 19B is a sectional view of the working end of FIG. 19A showing expansion of the dielectric membrane with an inflation medium to expand the membrane in a second direction.

FIGS. 18 and 19A-19B schematically illustrate another embodiment of working end 700 and a method of use. FIG. 18 is a transparent plan view of an expandable dielectric member or membrane 705 carried at distal end of introducer 710 that extends along longitudinal axis 715. The working end 700 is similar to previously described embodiments, which includes an expandable-collapsible frame of a spring material disposed within a fluid-tight interior chamber 716 of an elastic dielectric member 705. In one embodiment the frame comprises flexible outward frame elements 718*a* and 718*b* that can bow outwardly from a linear shape having a width W to an intermediate shape with width W' to a fully expanded shape with width W" as shown in FIG. 18. The outward frame elements 718*a* and 718*b* are flexed outwardly by distal movement of inner frame elements 720*a* and 720*b* that are coupled at proximal ends 722*a* and 722*b* to slidable inner sleeve 724. It can be understood from FIG. 18 that the distal tips of inner frame elements 720*a* and 720*b* are welded to distal tips of outward frame elements 718*a* and 718*b*, respectively as indicated by welds 728*a* and 728*b*. The frame elements are thus configured to provide lateral expansion forces to expand the dielectric member 705 and its ablation surface 730 (FIG. 19A) laterally relative to axis 715.

FIGS. 19A-19B illustrate another aspect of the invention wherein the working end 700, and more particularly the dielectric member 705, can be expanded in a second direction relative to axis 715 that is transverse to plane P of the frame expansion. Stated another way, the probe working end can be expanded anteriorly-posteriorly in the uterine cavity. FIG. 19A shows the dielectric membrane 705 stretched and expanded laterally in a first direction by the frame elements as in FIG. 18. FIG. 19B shows the dielectric membrane 705 further expanded in the second direction by inflation of the interior chamber 716 by means of a pressured inflow of gas from a gas inflow source 735 that is in communication with the interior chamber. In one embodiment, the gas flow into the dielectric member 705 comprises the Argon gas inflow that can be ionized as described previously to enable the electrosurgical energy delivery aspects of the invention.

Referring to FIG. 19B, it has been found that positive pressure in the interior chamber 716 during operation is useful in ablating tissue since the positive pressure can help maintain the ablation surface 730 in contact with tissue, which in turn permits more effective capacitive coupling through the dielectric membrane 705 and more effective passive conductive heating from the membrane 705 which is heated by ion bombardment from the contained plasma following the plasma formation in the interior chamber 716. In one embodiment, the pressure in the balloon is at least 20 mm Hg, at least 30 mm Hg, at least 40 mm Hg or at least 50 mm Hg (above ambient). Since the Argon gas is circulating as described above, the gas inflow rate and gas outflow rate can be modulated with valve assemblies and a controller to provide a predetermined net positive pressure in the interior chamber. It also has been found that positive pressure in the interior chamber 716 can be useful in causing plasma filaments to be more uniform and more widely dispersed since the dielectric membrane 705 may be spaced away from the frame elements 720a and 720b in the central region of the interior chamber.

Figure 20:
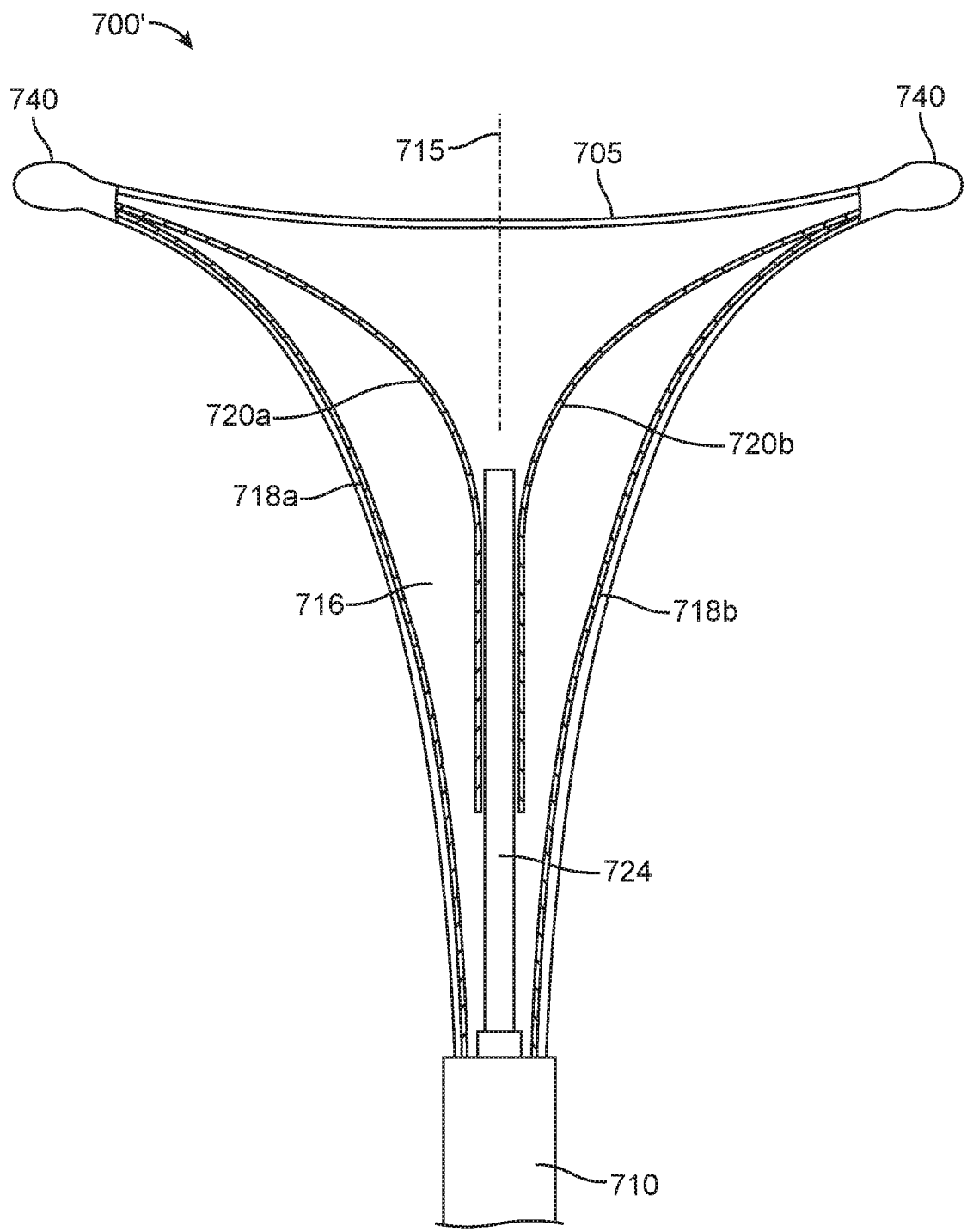
FIG. 20 is a cut-away view of another working end showing the dielectric membrane molded with soft distal tips.

FIG. 20 illustrates another aspect of the invention is which working end 700' has a dielectric membrane 705 has a triangular shape that is molded to provide soft, bulbous tips 740 at each distal apex of the membrane which assist in atraumatic introduction of the working end into the uterine cavity. In one variation, the tips 740 are soft silicone has have a thickness overlying the frame elements of at least 0.020", at least 0.040", or at least 0.060". The tip can have an elongated bulb or oval shape. In one variation, the tips can be flattened on the interior sides to adjoin one other when the frame is in a linear configuration for trans-cervical introduction (see shape W in FIG. 18).

Figure 21:
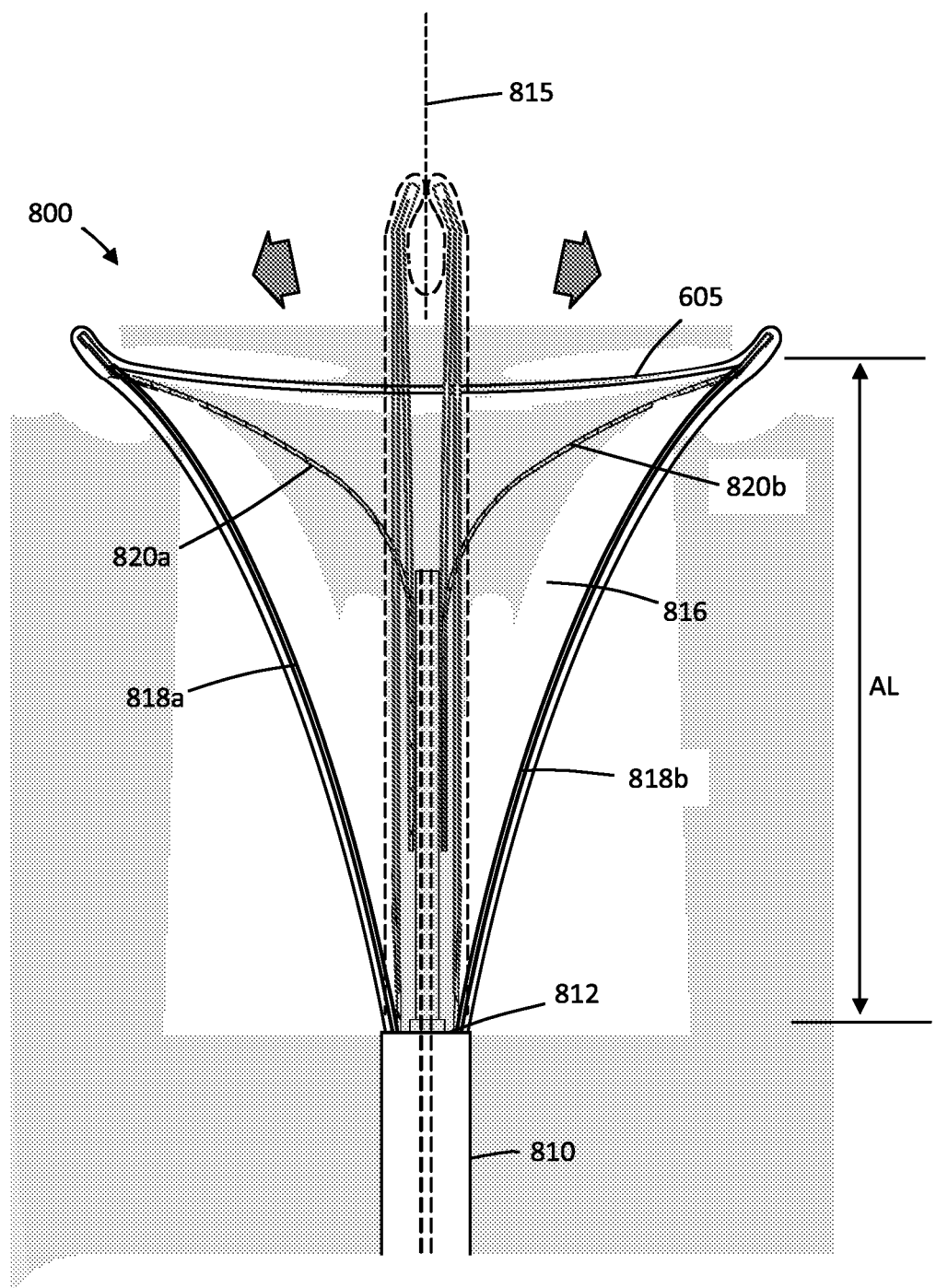
FIG. 21 is a sectional view of another working end that illustrate (i) the dissimilar properties of inner and outer frame elements used to expand the dielectric membrane, and (ii) the modified shape of the dielectric membrane provided by such frame elements.

FIG. 21 illustrates another embodiment of working end similar to those described previously with a dielectric membrane that can be expanded by frame that uses frame element with dissimilar spring characteristics to alter the expanded plan shape or the dielectric membrane structure to correspondingly increase the surface area of the energy delivery surface (for any given axial length of the dielectric membrane) to optimize energy delivery to engaged tissue. In FIG. 21, the working end 800 carries an expandable dielectric structure or membrane 805 at the distal end of introducer 810. The dielectric membrane is shown in a selected expanded shape having an axial length AL. It should be appreciated that the axial length can be adjusted between about 4 cm and 6.5 cm by controlling the length of the frame and dielectric membrane 805 that is permitted to extend outward from the distal end 812 of introducer sleeve 810 along longitudinal axis 815. The working end 800 is similar to previously described embodiments, wherein the expandable-collapsible frame is fabricated of a spring material disposed within the fluid-tight interior chamber 816 of the dielectric membrane 805. In one variation, the flexible outward frame elements 818a and 818b flex and bow outwardly from a linear non-deployed shape when actuated by inner frame elements 820a and 820b that are coupled at proximal ends 822a and 822b to slidable inner sleeve 824. The outer frame elements 818a and 818b are thus configured to directly engage the dielectric and apply lateral expanding forces to expand the dielectric membrane 805 and its ablation surface 830 to contact endometrial tissue. In one variation, referring to FIG. 21, the outer frame elements 818a and 818b can be 304 SS or 316 SS with a thickness of less than 0.012" and a width ranging between 2.5 mm and 5.0 mm.

The inner frame elements 820a and 820b are a dissimilar material that is configured to actuate and flex the outer frame elements and therefore has a thickness greater than 0.012". The outer elements can have a thickness ranging between 0.004" and 0.012". In one variation, the inner frame elements 820a and 820b have a thickness in the range of 0.012" to 0.020". In one variation, the inner frame elements 820a and 820b are 0.018" thickness NanoFlex® material manufactured by Sandvik Materials Technology, Åsgatan 1 SE-81181, Sandviken, Sweden.Sandvik's Nanoflex is a precipitation hardenable stainless steel specifically designed for applications requiring high strength, an absence of softening after exposure to high temperatures, and excellent weldability. The use of the dissimilar frame materials allows for the frame to expand as shown in FIG. 21 with lateral sides being relatively linear instead of being deeply bowed inwardly. Thus, the more triangular shape allows for an increased total surface area of the dielectric in contact with tissue when compared with a variation that has more deeply bowed outer frame elements (cf. FIG. 20).

In general, the endometrial ablation device comprises an elongated shaft with a working end having an axis and comprising a compliant energy-delivery surface (of the dielectric) actuatable by an interior expandable-contractible frame, the surface being expandable to a selected planar triangular shape configured for deployment to engage the walls of a patient's uterine cavity, and wherein the frame has flexible outer elements in lateral contact with the compliant surface and flexible inner elements not in said lateral contact, wherein the inner and outer elements have substantially dissimilar material properties. In this variation, the energy-delivery surface is configured for primary expansion in a lateral direction by the frame wherein axial movement of the inner elements moves the outer elements laterally. In this variation, the inner frame elements have a higher spring constant than the outer frame elements. In this variation, the inner frame elements have a plastic deformation range greater than the outer frame elements. In this variation, the inner frame elements are configured to maintain their spring function at operating temperatures of the system.

In another variation, an endometrial ablation device comprises an elongated shaft with a working end having an axis and comprising a compliant energy-delivery surface actuatable by an interior expandable-contractible frame, the surface being expandable to a selected planar triangular shape configured for deployment to engage the walls of a patient's uterine cavity, and wherein the selected shape can have an axial length ranging at least between 4.5 cm and 6.5 cm. In this variation, the selected shape can have a width between a first apex and second apex ranging at least between 2.5 cm and 5 cm.

In one embodiment of working end, the compliant surface comprises a dielectric with a surface area of at least 25 $cm^2$. This embodiment can a surface area ranging at least between 25 $cm^2$ and 30 $cm^2$.

In one variation of working end, the compliant surface has a surface area of at least 22 $cm^2$ when the selected length is 4.0 cm. In this variation, the compliant surface has a surface area of at least 23 $cm^2$ when the selected length is 4.5 cm. In this variation, the compliant surface has a surface area of at least 24 $cm^2$ when the selected length is 5.0 cm. In this variation, the compliant surface has a surface area of at least 25 $cm^2$ when the selected length is 5.5 cm. In this variation, the compliant surface has a surface area of at least 26 $cm^2$ when the selected length is 6.0 cm. In this variation, the compliant surface has a surface area of at least 27 $cm^2$ when the selected length is 6.5 cm.

In another variation of working end, the compliant surface has a ratio of "surface area to axial length" of at least 4.5:1 in any selected axial length ranging from 4.5 cm to 6.5 cm.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are present in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modification and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for endometrial ablation comprising:
   expanding a frame within a compliant energy-delivery surface to cause the surface to assume a planar triangular shape having distal apices to engage the walls of a patient's uterine cavity;
   wherein the frame has flexible outer elements in lateral contact with the compliant surface and flexible inner elements not in said lateral contact, wherein the flexible inner elements and the outer flexible elements have substantially dissimilar material properties to cause lateral sides of the frame to become relatively linear and less bowed inward.

2. The method of claim 1, wherein the compliant energy-delivery surface is configured for primary expansion in a lateral direction by the frame wherein axial movement of the flexible inner elements moves portions of the flexible outer elements laterally.

3. The method of claim 1, wherein the flexible inner elements have a higher spring constant than the outer flexible elements.

4. The method of claim 1, wherein the flexible inner elements have a plastic deformation range greater than the flexible outer elements.

5. The method of claim 1, wherein the flexible inner elements are configured to maintain their spring function at operating temperatures.

6. The method of claim 1, wherein the flexible inner elements are formed from a precipitation hardenable stainless steel.

7. The method of claim 1, wherein the flexible outer elements are 304 SS or 316 SS.

8. The method of claim 1, wherein the flexible inner elements have a thickness greater than 0.012".

9. The method of claim 1, wherein the flexible outer elements have a thickness less than 0.012".

10. The method of claim 1, wherein the flexible inner elements have a thickness ranging between 0.0012" and 0.020".

11. The method of claim 1, wherein the flexible outer elements have a thickness ranging between 0.004" and 0.012".

12. The method of claim 1, wherein outer and inner elements of the frame are fixed to one another at an apex and a dielectric material overlies said apex.

13. The method of claim 12, wherein said dielectric material has a thickness in the range from 0.005" to 0.025".

14. A method for endometrial ablation comprising:
introducing a collapsed, compliant energy-delivery surface and frame transcervically into a patient's uterine cavity;
expanding the frame within the compliant energy-delivery surface to cause the surface to assume a planar triangular shape to engage the walls of a patient's uterine cavity, wherein the frame comprises flexible inner elements and outer flexible elements which have substantially dissimilar material properties to cause lateral sides of the frame to become relatively linear and less bowed inward;
wherein said compliant energy-delivery surface when in the planar triangular shape includes axial lengths ranging between 4.5 cm and 6.5 cm; and
delivering energy from the energy-delivery surface to ablate tissue.

15. The method of claim 14, wherein the planar triangular shape has a width between a first apex and second apex ranging between 2.5 cm and 5 cm.

16. The method of claim 14, wherein the compliant surface is configured for primary expansion laterally outward from the axis by the frame.

17. The method of claim 14, wherein the compliant surface has a surface area of at least 25 cm$^2$.

18. The method of claim 14, wherein the compliant surface has a surface area ranging at least between 25 cm$^2$ and 30 cm$^2$.

19. The method of claim 14, wherein the compliant surface has a surface area of at least 22 cm$^2$ when the selected length is 4.0 cm.

20. The method of claim 14, wherein the compliant surface has a surface area of at least 23 cm$^2$ when the selected length is 4.5 cm.

21. The method of claim 14, wherein the compliant surface has a surface area of at least 24 cm$^2$ when the selected length is 5.0 cm.

22. The method of claim 14, wherein outer and inner elements of the frame are fixed to one another at an apex and a dielectric material overlies said apex.

23. The method of claim 22, wherein said dielectric material has a thickness in the range from 0.005" to 0.025".

* * * * *